United States Patent [19]
Usami et al.

[11] Patent Number: 5,973,158
[45] Date of Patent: Oct. 26, 1999

[54] HEPTAMETHINE CYANINE COMPOUND, NEAR INFRARED ABSORBING INK, NEAR INFRARED ABSORBING SHEET AND SILVER HALIDE PHOTOGRAPHIC MATERIAL

[75] Inventors: Takashi Usami; Junji Nishigaki, both of Kanagawa, Japan

[73] Assignee: Fuji Photo Film Co., Ltd., Kanagawa, Japan

[21] Appl. No.: 09/024,895

[22] Filed: Feb. 17, 1998

[30] Foreign Application Priority Data

Feb. 17, 1997 [JP] Japan ................................. 9-048442

[51] Int. Cl.[6] ........................ C09B 23/08; C07D 410/14; C07D 413/14; C07D 417/14
[52] U.S. Cl. ..................... 546/270.1; 546/273.4; 546/277.4
[58] Field of Search .............. 546/270.1, 273.4, 546/277.4

[56] References Cited

U.S. PATENT DOCUMENTS 4,847,385  7/1989  Kusakata et al. ................. 548/455
5,260,178  11/1993 Harada et al. ..................... 430/508
5,714,307  2/1998  Harada et al. ..................... 430/390

*Primary Examiner*—Fiona T. Powers
*Attorney, Agent, or Firm*—Birch, Stewart, Kolasch & Birch, LLP

[57] ABSTRACT

A heptamethine cyanine compound is represented by the formula (I):

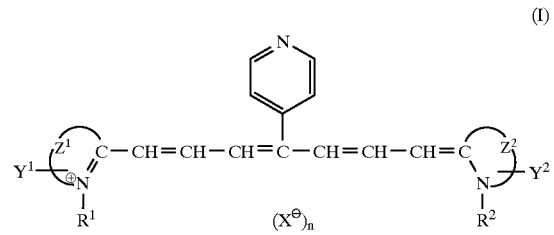

in which each of $Z^1$ and $Z^2$ is an atomic group that forms a five or six-membered heterocyclic ring or a five or six-membered heterocyclic ring condensed with benzene ring or naphthalene ring; each of $R^1$ and $R^2$ is an alkyl group or a substituted alkyl group; each of $Y^1$ and $Y^2$ is carboxyl, a sulfonamido group or a sulfamoyl group; X is an anion; and n is 0 or 1. The present specification also discloses a near infrared absorbing ink, a near infrared absorbing sheet and a silver halide photographic material using the heptamethine cyanine compound as a near infrared absorbing dye.

13 Claims, 3 Drawing Sheets

HEPTAMETHINE CYANINE COMPOUND, NEAR INFRARED ABSORBING INK, NEAR INFRARED ABSORBING SHEET AND SILVER HALIDE PHOTOGRAPHIC MATERIAL

FIELD OF THE INVENTION

The present invention relates to a heptamethine cyanine compound. The invention also relates to a near infrared absorbing ink, a near infrared absorbing sheet and a silver halide photographic material using the heptamethine cyanine compound as a near infrared absorbing dye.

BACKGROUND OF THE INVENTION

Various optical, photographic or printing materials use a near infrared absorbing dye. The near infrared absorbing dye has an absorption maximum ($\lambda$max) within the near infrared region (900 to 1,100 nm). An ideal near infrared absorbing dye has no absorption within the visible region (400 to 600 nm).

An appropriate tool such as an infrared sensor can easily notice a near infrared ray, though the naked eye cannot see it. If an ink contains the ideal near infrared absorbing dye having no absorption within the visible region, the ink can record invisible information (character, image or the like) without disturbing visible information.

A sheet containing a near infrared absorbing dye is sometimes used as an optical filter. The near infrared absorbing sheet can substantially be transparent by using the ideal near infrared absorbing dye.

A silver halide photographic material is usually treated in an automatic developing machine. The machine has an infrared sensor of detecting the photographic material to conduct photographic treatment automatically. Japanese Patent Provisional Publication Nos. 1(1989)-266536, 3(1991)-226736 and European Patent No. 0703494A1 propose adding a near infrared absorbing dye to a silver halide photographic material to improve precision in detection of the material. Further, a near infrared sensitive silver halide photographic material should contain a near infrared absorbing dye as an antihalation dye, as is described in Japanese Patent Provisional Publication No. 63(1988)-55544. The near infrared absorbing dye used in a silver halide photographic material also preferably is an ideal dye having no absorption within the visible region to avoid influence on the exposure of light within the visible region or on the formed visible image.

Japanese Patent Provisional Publication Nos. 63(1988)-55544, 1(1989)-266536, 3(1991)-226736 and European Patent No. 0703494A1 disclose various near infrared absorbing dyes. However, the known near infrared absorbing dyes have remarkable absorption within the visible region.

The absorption maximum ($\lambda$max) of a dye in the form of specific aggregates is longer than that of the same dye contained in a solution. This phenomenon about J aggregates of a spectral sensitizing dye used in silver halide photographic material is reported in H. T. James, The Theory of the Photographic Process, Macmillan Publishing Co., Inc., (1977), pages 218 to 222. If a near infrared absorbing dye is used in the form of specific aggregates, the absorption within the visible region (shorter than the infrared region) is reduced.

Even though the known near infrared absorbing dyes are used in the form of aggregates, the dyes still have remarkable absorption within the visible region.

SUMMARY OF THE INVENTION

An object of the present invention is to provide a heptamethine cyanine compound preferably used as a near infrared absorbing dye.

Another object of the invention is to provide a near infrared absorbing ink, a near infrared absorbing sheet and a silver halide photographic material using a near infrared absorbing dye having substantially no absorption within the visible region.

The present invention provides a heptamethine cyanine compound represented by the formula (I):

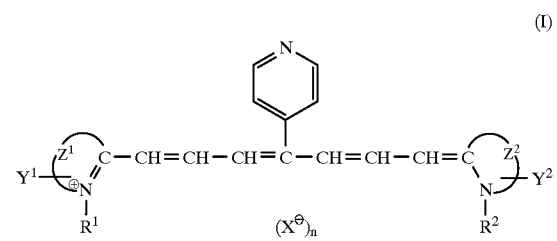

in which each of $Z^1$ and $Z^2$ independently is an atomic group that forms a five or six-membered heterocyclic ring or a five or six-membered heterocyclic ring condensed with benzene ring or naphthalene ring; each of $R^1$ and $R^2$ independently is an alkyl group having 1 to 20 carbon atoms or a substituted alkyl group having 1 to 20 carbon atoms; each of $Y^1$ and $Y^2$ independently is a substituent group which is selected from the group consisting of carboxyl, a sulfonamido group having 1 to 20 carbon atoms and a sulfamoyl group having 0 to 20 carbon atoms; X is an anion; and n is 0 or 1.

The invention also provides a near infrared absorbing ink in which a near infrared absorbing dye is dissolved or dispersed in a liquid medium, wherein the infrared absorbing dye is the heptamethine cyanine compound represented by the formula (I).

The invention further provides a near infrared absorbing sheet comprising a transparent support and a near infrared absorbing layer containing a near infrared absorbing dye and a binder, wherein the infrared absorbing dye is the heptamethine cyanine compound represented by the formula (I).

The invention furthermore provides a silver halide photographic material comprising a support, a silver halide emulsion layer and a non-light-sensitive hydrophilic colloidal layer, wherein the silver halide emulsion layer or the non-light-sensitive hydrophilic colloidal layer contains the heptamethine cyanine compound represented by the formula (I) as a near infrared absorbing dye.

DETAILED DESCRIPTION OF THE INVENTION

Figure 1:
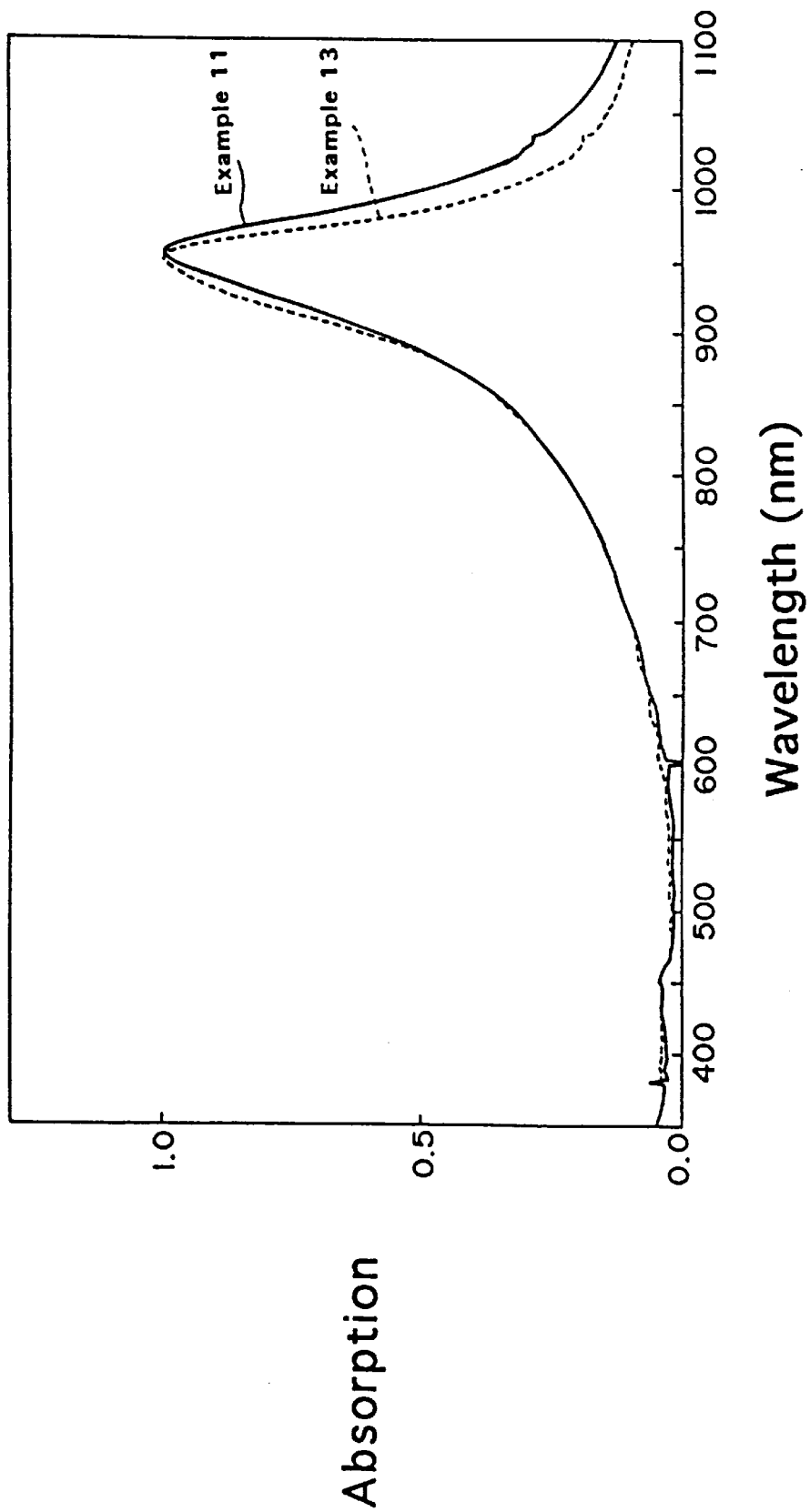
FIG. 1 is a graph showing absorption spectra of near infrared absorbing sheets prepared in Examples 11 and 13.

The heptamethine cyanine compound of the present invention is represented by the following formula (I).

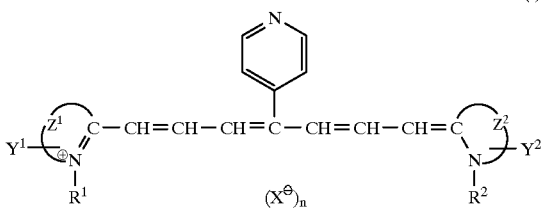

(I)

In the formula (I), each of $Z^1$ and $Z^2$ independently is an atomic group that forms a five or six-membered heterocyclic ring. Examples of the five or six-membered heterocyclic rings include pyrrole ring, imidazole ring, oxazole ring, thiazole ring, selenazole ring and pyridine ring. A five-membered ring is preferred to a six-membered ring.

The five or six-membered heterocyclic ring may be condensed with benzene ring or naphthalene ring. Examples of the condensed rings include indole ring, benzimidazole ring, benzoxazole ring, benzothiazole ring, benzoselenazole ring, benzindole ring, naphthimidazole ring, naphthoxazole ring, naphthothiazole ring, naphthoselenazole ring and quinoline ring. A five-membered heterocyclic ring condensed with benzene ring is particularly preferred.

The five or six-membered heterocyclic ring and the benzene or naphthalene ring may have a substituent group (other then $Y^1$ and $Y^2$) Examples of the substituent groups include an alkyl group having 1 to 20 carbon atoms and a substituted alkyl group having 1 to 20 carbon atoms. The details of the alkyl group and the substituted alkyl group are the same as those of $R^1$ and $R^2$ described below.

In the formula (I), each of $R^1$ and $R^2$ independently is an alkyl group having 1 to 20 carbon atoms or a substituted alkyl group having 1 to 20 carbon atoms.

The alkyl group preferably has 1 to 15 carbon atoms, more preferably has 1 to 10 carbon atoms, and most preferably has 1 to 5 carbon atoms. A chain alkyl group is preferred to a cyclic alkyl group. An alkyl group of a straight chain (normal alkyl group) is particularly preferred.

The details of the alkyl moiety of the substituted alkyl group are the same as those of the alkyl group described above. An example of the substituent group of the substituted alkyl group is sulfo. Sulfo may form a salt with a cation.

In the formula (I), each of $Y^1$ and $y^2$ independently is a substituent group of the five or six-membered heterocyclic ring, the condensed benzene ring or the condensed naphthalene ring, and preferably is a substituent group of the condensed benzene ring or the condensed naphthalene ring.

Each of $Y^1$ and $Y^2$ independently is selected from the group consisting of carboxyl, a sulfonamido group having 1 to 20 carbon atoms and a sulfamoyl group having 0 to 20 carbon atoms. The proton of carboxyl may be dissociated. The sulfonamido group is represented by —NHSO$_2$R, wherein R is an alkyl group having 1 to 20 carbon atoms, a substituted alkyl group having 1 to 20 carbon atoms, an aryl group having 6 to 20 carbon atoms or a substituted aryl group having 6 to 20 carbon atoms. The sulfamoyl group is represented by —SO$_2$NHR, wherein R is hydrogen, an alkyl group having 1 to 20 carbon atoms, a substituted alkyl group having 1 to 20 carbon atoms, an aryl group having 6 to 20 carbon atoms or a substituted aryl group having 6 to 20 carbon atoms.

In the formula (I), X is an anion, and preferably is a monovalent anion. Examples of the monovalent anions include halide ion (e.g., Cl$^-$, Br$^-$, I$^-$), p-toluenesulfonate ion, PF$_6^-$, BF$_4^-$ and ClO$_4^-$.

In the formula (I), n is 0 or 1. When the compound forms an intramolecular salt, n is 0.

A preferred heptamethine cyanine compound is represented by the following formula (IIa), (IIb) or (IIc).

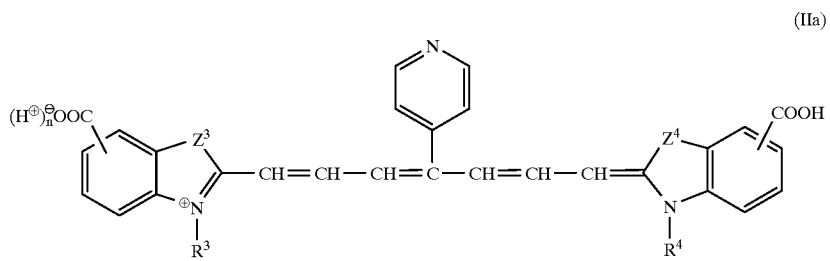

(IIa)

In the formula (IIa), each of $Z^3$ and $Z^4$ independently is —CR$^5$R$^6$—, —NR$^7$—, —O—, —S— or —Se—, preferably is —CR$^5$R$^6$—, —NR$^7$—, —O— or —S—, more preferably is —CR$^5$R$^6$—, —O— or —S—, further preferably is —CR$^5$R$^6$— or —O—, and most preferably is —CR$^5$R$^6$—. Each of R$^5$, R$^6$ and R$^7$ independently is an alkyl group having 1 to 5 carbon atoms. A chain alkyl group is preferred to a cyclic alkyl group. An alkyl group of a straight chain (normal alkyl group) is particularly preferred.

In the formula (IIa), R$^3$ is an alkyl group having 1 to 20 carbon atoms or a sulfoalkyl group having 1 to 20 carbon atoms.

The alkyl group preferably has 1 to 15 carbon atoms, more preferably has 1 to 10 carbon atoms, and most preferably has 1 to 5 carbon atoms. A chain alkyl group is preferred to a cyclic alkyl group. An alkyl group of a straight chain (normal alkyl group) is particularly preferred.

The details of the alkyl moiety of the sulfoalkyl group are the same as those of the alkyl group described above. The proton of sulfo is usually dissociated.

In the formula (IIa), R$^4$ is an alkyl group having 1 to 20 carbon atoms or a salt of a sulfoalkyl group having 1 to 20 carbon atoms. The details of the alkyl group and the alkyl moiety of the sulfoalkyl are the same as those of the alkyl group of R$^3$ described above.

When R$^3$ is an alkyl group, R$^4$ preferably is an alkyl group. When R$^3$ is a sulfoalkyl group, R$^4$ preferably is a salt of a sulfoalkyl group. A cation forming the salt of the sulfoalkyl group preferably is monovalent. Examples of the monovalent cations include alkali metal ions (e.g., Na$^+$, K$^+$).

In the formula (IIa), n is 0 when R$^3$ is an alkyl group, and n is 1 when R$^3$ is a sulfoalkyl group.

(IIb)

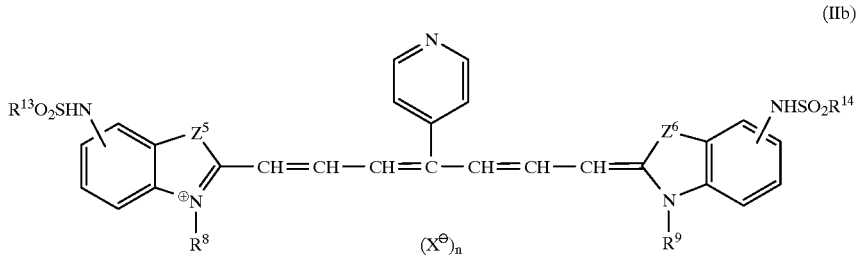

In the formula (IIb), each of $Z^5$ and $Z^6$ independently is $-CR^{10}R^{11}-$, $-NR^{12}-$, $-O-$, $-S-$ or $-Se-$, preferably is $-CR^{10}R^{11}$, $-NR^{12}-$, $-O-$ or $-S-$, more preferably is $-CR^{10}R^{11}-$, $-O-$ or $-S$, further preferably is $-CR^{10}R^{11}-$ or $-O-$, and most preferably is $-CR^{10}R^{11}-$. Each of $R^{10}$, $R^{11}$ and $R^{12}$ independently is an alkyl group having 1 to 5 carbon atoms. A chain alkyl group is preferred to a cyclic alkyl group. An alkyl group of a straight chain (normal alkyl group) is particularly preferred.

In the formula (IIb), $R^8$ is an alkyl group having 1 to 20 carbon atoms or a sulfoalkyl group having 1 to 20 carbon atoms.

The alkyl group preferably has 1 to 15 carbon atoms, more preferably has 1 to 10 carbon atoms, and most preferably has 1 to 5 carbon atoms. A chain alkyl group is preferred to a cyclic alkyl group. An alkyl group of a straight chain (normal alkyl group) is particularly preferred.

The details of the alkyl moiety of the sulfoalkyl group are the same as those of the alkyl group described above. The proton of sulfo is usually dissociated.

In the formula (IIb), $R^9$ is an alkyl group having 1 to 20 carbon atoms or a salt of a sulfoalkyl group having 1 to 20 carbon atoms. The details of the alkyl group and the alkyl moiety of the sulfoalkyl are the same as those of the alkyl group of $R^8$ described above.

When $R^8$ is an alkyl group, $R^9$ preferably is an alkyl group. When $R^8$ is a sulfoalkyl group, $R^9$ preferably is a salt of a sulfoalkyl group. A cation forming the salt of the sulfoalkyl group preferably is monovalent. Examples of the monovalent cations include alkali metal ions (e.g., $Na^+$, $K^+$).

In the formula (IIb), each of $R^{13}$ and $R^{14}$ independently is an alkyl group having 1 to 20 carbon atoms.

The alkyl group preferably has 1 to 15 carbon atoms, more preferably has 1 to 10 carbon atoms, and most preferably has 1 to 5 carbon atoms. A chain alkyl group is preferred to a cyclic alkyl group. An alkyl group of a straight chain (normal alkyl group) is particularly preferred.

In the formula (IIb), X is an anion, and preferably is a monovalent anion. Examples of the monovalent anions include halide ion (e.g., $Cl^-$, $Br^-$, $I^-$), p-toluenesulfonate ion, $PF_6^-$, $BF_4^-$ and $ClO_4^-$.

In the formula (IIb), n is 1 when $R^8$ is an alkyl group, and n is 0 when $R^8$ is a sulfoalkyl group.

(IIc)

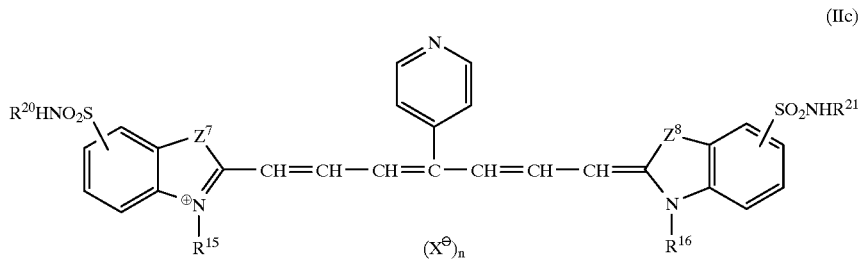

In the formula (IIc), each of $Z^7$ and $Z^8$ independently is $-CR^{17}R^{18}-$, $-NR^{19}-$, $-O-$, $-S-$ or $-Se-$, preferably is $-CR^{17}R^{18}$, $-NR^{19}-$, $-O-$ or $-S-$, more preferably is $-CR^{17}R^{18}-$, $-O-$ or $-S$, further preferably is $-CR^{17}R^{18}-$ or $-O-$, and most preferably is $-CR^{17}R^{18}-$. Each of $R^{17}$, $R^{18}$ and $R^{19}$ independently is an alkyl group having 1 to 5 carbon atoms. A chain alkyl group is preferred to a cyclic alkyl group. An alkyl group of a straight chain (normal alkyl group) is particularly preferred.

In the formula (IIc), $R^{15}$ is an alkyl group having 1 to 20 carbon atoms or a sulfoalkyl group having 1 to 20 carbon atoms.

The alkyl group preferably has 1 to 15 carbon atoms, more preferably has 1 to 10 carbon atoms, and most preferably has 1 to 5 carbon atoms. A chain alkyl group is preferred to a cyclic alkyl group. An alkyl group of a straight chain (normal alkyl group) is particularly preferred.

The details of the alkyl moiety of the sulfoalkyl group are the same as those of the alkyl group described above. The proton of sulfo is usually dissociated.

In the formula (IIc), $R^{16}$ is an alkyl group having 1 to 20 carbon atoms or a salt of a sulfoalkyl group having 1 to 20 carbon atoms. The details of the alkyl group and the alkyl moiety of the sulfoalkyl are the same as those of the alkyl group of $R^{15}$ described above.

When $R^{15}$ is an alkyl group, $R^{16}$ preferably is an alkyl group. When $R^{15}$ is a sulfoalkyl group, $R^{16}$ preferably is a salt of a sulfoalkyl group. A cation forming the salt of the sulfoalkyl group preferably is monovalent. Examples of the monovalent cations include alkali metal ions (e.g., $Na^+$, $K^+$).

In the formula (IIc), each of $R^{20}$ and $R^{21}$ independently is an alkyl group having 1 to 20 carbon atoms.

The alkyl group preferably has 1 to 15 carbon atoms, more preferably has 1 to 10 carbon atoms, and most preferably has 1 to 5 carbon atoms. A chain alkyl group is preferred to a cyclic alkyl group. An alkyl group of a straight chain (normal alkyl group) is particularly preferred.

In the formula (IIc), X is an anion, and preferably is a monovalent anion. Examples of the monovalent anions include halide ion (e.g., $Cl^-$, $Br^-$, $I^-$), p-toluenesulfonate ion, $PF_6^-$, $BF_4^-$ and $ClO_4^-$.

In the formula (IIc), n is 1 when $R^{15}$ is an alkyl group, and n is 0 when $R^{15}$ is a sulfoalkyl group.

A more preferred heptamethine cyanine compound is represented by the formula (IIIa), (IIIb) or (IIIc).

In the formula (IIIb), $R^{24}$ is an alkyl group having 1 to 5 carbon atoms or a sulfoalkyl group having 1 to 5 carbon atoms. A chain alkyl group is preferred to a cyclic alkyl group. An alkyl group of a straight chain (normal alkyl group) is particularly preferred. The details of the alkyl moiety of the sulfoalkyl group are the same as those of the alkyl group described above. The proton of sulfo is usually dissociated.

In the formula (IIIb), $R^{25}$ is an alkyl group having 1 to 5 carbon atoms or a salt of a sulfoalkyl group having 1 to 5 carbon atoms. The details of the alkyl group and the alkyl moiety of the sulfoalkyl are the same as those of the alkyl group of $R^{24}$ described above.

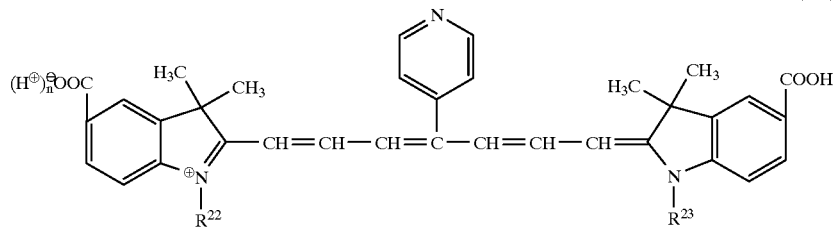

(IIIa)

In the formula (IIIa), $R^{22}$ is an alkyl group having 1 to 5 carbon atoms or a sulfoalkyl group having 1 to 5 carbon atoms. A chain alkyl group is preferred to a cyclic alkyl group. An alkyl group of a straight chain (normal alkyl group) is particularly preferred. The details of the alkyl moiety of the sulfoalkyl group are the same as those of the alkyl group described above. The proton of sulfo is usually dissociated.

In the formula (IIIa), $R^{23}$ is an alkyl group having 1 to 5 carbon atoms or a salt of a sulfoalkyl group having 1 to 5 carbon atoms. The details of the alkyl group and the alkyl moiety of the sulfoalkyl are the same as those of the alkyl group of $R^{22}$ described above.

When $R^{22}$ is an alkyl group, $R^{23}$ preferably is an alkyl group. When $R^{22}$ is a sulfoalkyl group, $R^{23}$ preferably is a salt of a sulfoalkyl group. A cation forming the salt of the sulfoalkyl group preferably is monovalent. Examples of the monovalent cations include alkali metal ions (e.g., $Na^+$, $K^+$).

In the formula (IIIa), n is 0 when $R^{22}$ is an alkyl group, and n is 1 when $R^{22}$ is a sulfoalkyl group.

When $R^{24}$ is an alkyl group, $R^{25}$ preferably is an alkyl group. When $R^{24}$ is a sulfoalkyl group, $R^{25}$ preferably is a salt of a sulfoalkyl group. A cation forming the salt of the sulfoalkyl group preferably is monovalent. Examples of the monovalent cations include alkali metal ions (e.g., $Na^+$, $K^+$).

In the formula (IIIb), each of $R^{26}$ and $R^{27}$ independently is an alkyl group having 1 to 5 carbon atoms. A chain alkyl group is preferred to a cyclic alkyl group. An alkyl group of a straight chain (normal alkyl group) is particularly preferred.

In the formula (IIIb), X is an anion, and preferably is a monovalent anion. Examples of the monovalent anions include halide ion (e.g., $Cl^-$, $Br^-$, $I^-$), p-toluenesulfonate ion, $PF_6^-$, $BF_4^-$ and $ClO_4^-$.

In the formula (IIIb), n is 1 when $R^{24}$ is an alkyl group, and n is 0 when $R^{24}$ is a sulfoalkyl group.

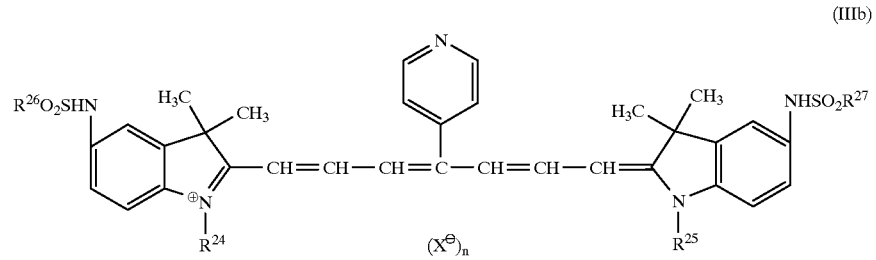

(IIIb)

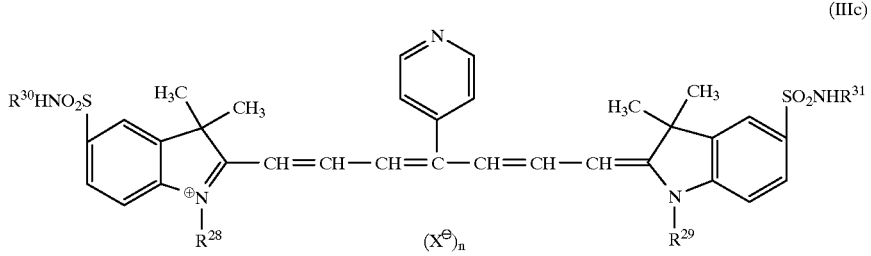

(IIIc)

In the formula (IIIc), $R^{28}$ is an alkyl group having 1 to 5 carbon atoms or a sulfoalkyl group having 1 to 5 carbon atoms. A chain alkyl group is preferred to a cyclic alkyl group. An alkyl group of a straight chain (normal alkyl group) is particularly preferred. The details of the alkyl moiety of the sulfoalkyl group are the same as those of the alkyl group described above. The proton of sulfo is usually dissociated.

In the formula (IIIc), $R^{29}$ is an alkyl group having 1 to 5 carbon atoms or a salt of a sulfoalkyl group having 1 to 5 carbon atoms. The details of the alkyl group and the alkyl moiety of the sulfoalkyl are the same as those of the alkyl group of $R^{28}$ described above.

When $R^{28}$ is an alkyl group, $R^{29}$ preferably is an alkyl group. When $R^{28}$ is a sulfoalkyl group, $R^{29}$ preferably is a salt of a sulfoalkyl group. A cation forming the salt of the sulfoalkyl group preferably is monovalent. Examples of the monovalent cations include alkali metal ions (e.g., $Na^+$, $K^+$).

In the formula (IIIc), each of $R^{30}$ and $R^{31}$ independently is an alkyl group having 1 to 5 carbon atoms. A chain alkyl group is preferred to a cyclic alkyl group. An alkyl group of a straight chain (normal alkyl group) is particularly preferred.

In the formula (IIIc), X is an anion, and preferably is a monovalent anion. Examples of the monovalent anions include halide ion (e.g., $Cl^-$, $Br^-$, $I^-$), p-toluenesulfonate ion, $PF_6^-$, $BF_4^-$ and $ClO_4^-$.

In the formula (IIIc), n is 1 when $R^{28}$ is an alkyl group, and n is 0 when $R^{28}$ is a sulfoalkyl group.

The most preferred heptamethine cyanine compound is represented by the formula (IVa), (IVb), (IVc), (IVd), (IVe) or (IVf).

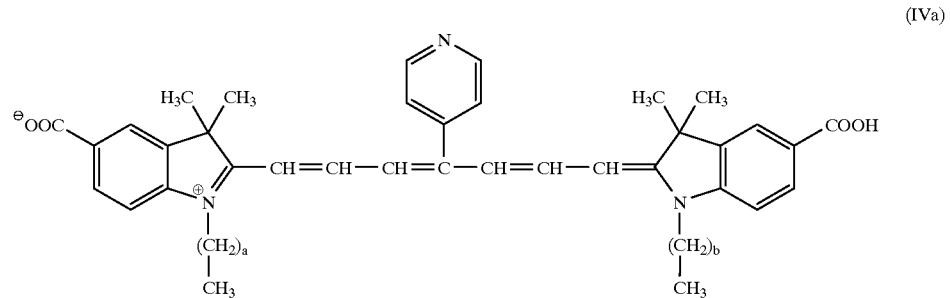

(IVa)

In the formula (IVa), each of a and b independently is 0, 1, 2, 3 or 4.

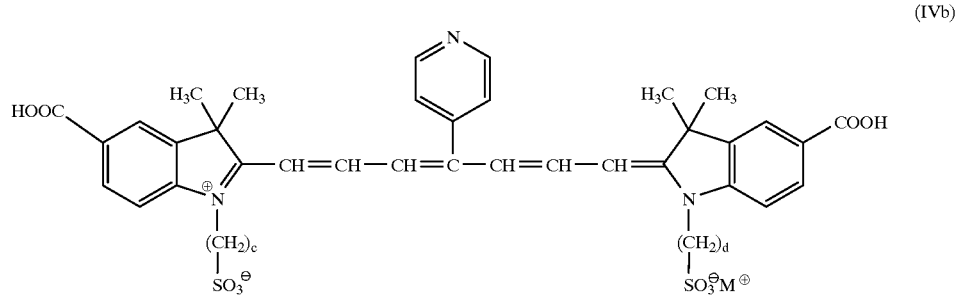

(IVb)

In the formula (IVb), each of c and d independently is 1, 2, 3, 4 or 5

In the formula (IVb), M is a monovalent cation.

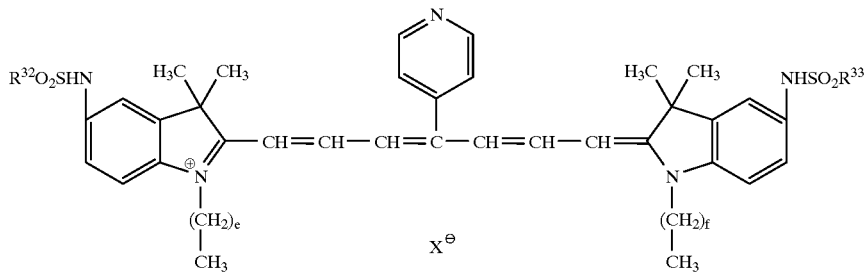

(IVc)

In the formula (IVc), each of e and f independently is 0, 1, 2, 3 or 4.

In the formula (IVc), X is a monovalent anion

In the formula (IVc), each of $R^{32}$ and $R^{33}$ independently is an alkyl group having 1 to 5 carbon atoms.

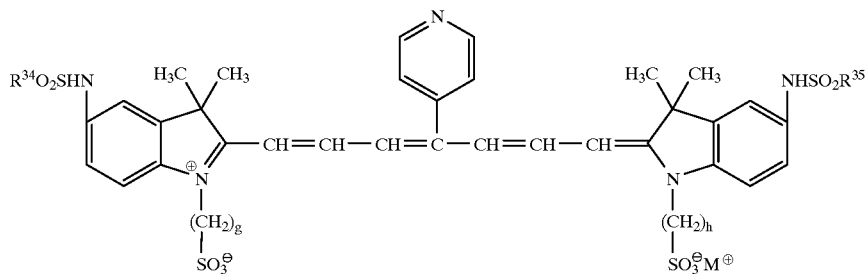

(IVd)

In the formula (IVd), each of g and h independently is 1, 2, 3, 4 or 5.

In the formula (IVd), m is a monovalent cation.

In the formula (IVd), each of $R^{34}$ and $R^{35}$ independently is an alkyl group having 1 to 5 carbon atoms.

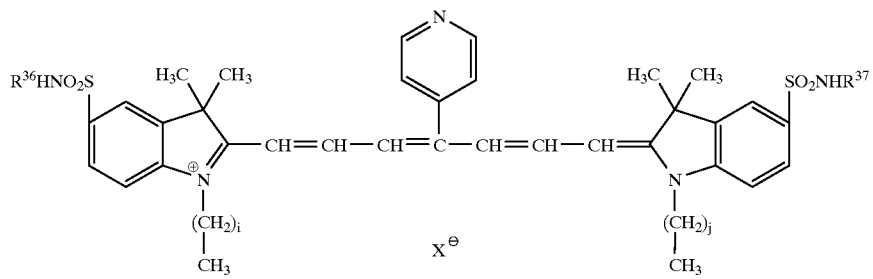

(IVe)

In the formula (IVe), each of i and j independently is 0, 1, 2, 3 or 4.

In the formula (IVe), X is a monovalent anion.

In the formula (IVe), each of $R^{36}$ and $R^{37}$ independently is an alkyl group having 1 to 5 carbon atoms.

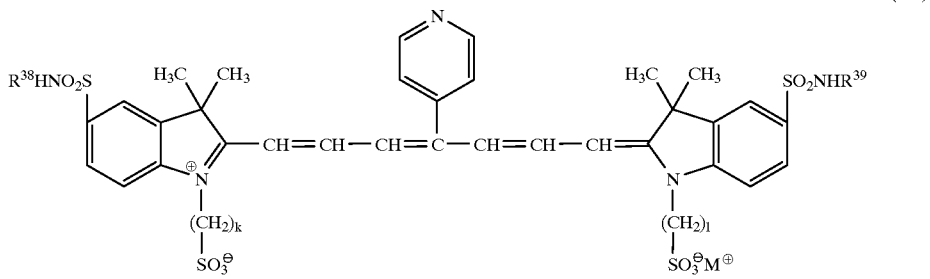

In the formula (IVf), each of k and l independently is 1, 2, 3, 4 or 5.

In the formula (IVf), M is a monovalent cation.

In the formula (IVf), each of $R^{38}$ and $R^{39}$ independently is an alkyl group having 1 to 5 carbon atoms.

Examples of the heptamethine cyanine compounds of the present invention are shown below.

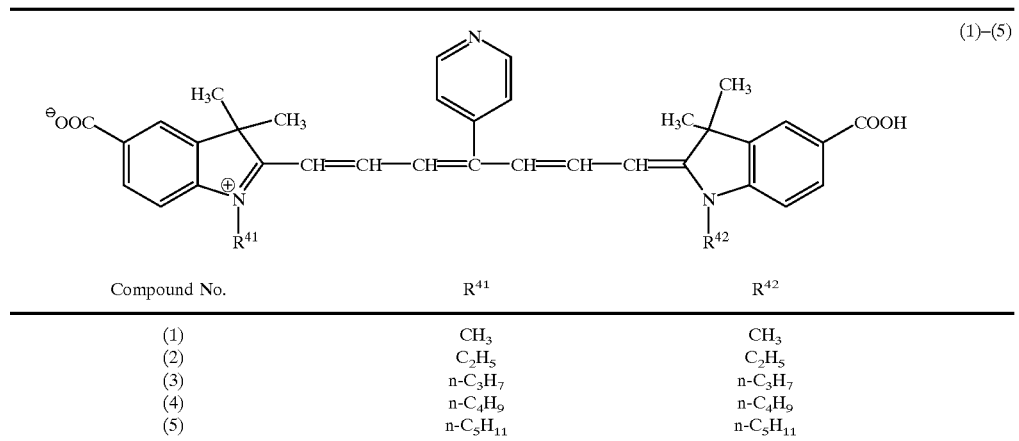

| Compound No. | $R^{41}$ | $R^{42}$ |
|---|---|---|
| (1) | $CH_3$ | $CH_3$ |
| (2) | $C_2H_5$ | $C_2H_5$ |
| (3) | n-$C_3H_7$ | n-$C_3H_7$ |
| (4) | n-$C_4H_9$ | n-$C_4H_9$ |
| (5) | n-$C_5H_{11}$ | n-$C_5H_{11}$ |

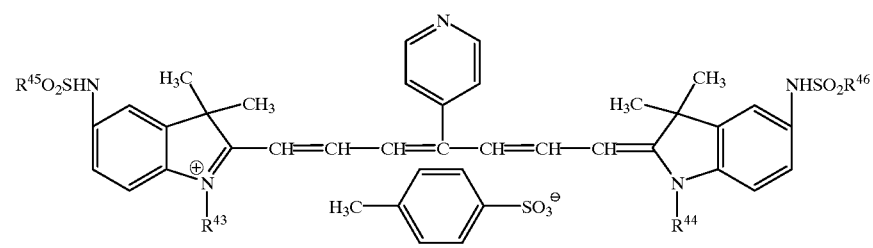

| No. | $R^{43}$ | $R^{44}$ | $R^{45}$ | $R^{46}$ |
|---|---|---|---|---|
| (6) | $CH_3$ | $CH_3$ | $CH_3$ | $CH_3$ |
| (7) | $CH_3$ | $CH_3$ | $C_2H_5$ | $C_2H_5$ |
| (8) | $CH_3$ | $CH_3$ | n-$C_3H_7$ | n-$C_3H_7$ |
| (9) | $CH_3$ | $CH_3$ | n-$C_4H_9$ | n-$C_4H_9$ |
| (10) | $C_2H_5$ | $C_2H_5$ | $CH_3$ | $CH_3$ |
| (11) | $C_2H_5$ | $C_2H_5$ | $C_2H_5$ | $C_2H_5$ |
| (12) | $C_2H_5$ | $C_2H_5$ | n-$C_3H_7$ | n-$C_3H_7$ |
| (13) | $C_2H_5$ | $C_2H_5$ | n-$C_4H_9$ | n-$C_4H_9$ |
| (14) | n-$C_3H_7$ | n-$C_3H_7$ | $CH_3$ | $CH_3$ |
| (15) | n-$C_3H_7$ | n-$C_3H_7$ | $C_2H_5$ | $C_2H_5$ |
| (16) | n-$C_3H_7$ | n-$C_3H_7$ | n-$C_3H_7$ | n-$C_3H_7$ |
| (17) | n-$C_3H_7$ | n-$C_3H_7$ | n-$C_4H_9$ | n-$C_4H_9$ |
| (18) | n-$C_4H_9$ | n-$C_4H_9$ | $CH_3$ | $CH_3$ |
| (19) | n-$C_4H_9$ | n-$C_4H_9$ | $C_2H_5$ | $C_2H_5$ |
| (20) | n-$C_4H_9$ | n-$C_4H_9$ | n-$C_3H_7$ | n-$C_3H_7$ |
| (21) | n-$C_4H_9$ | n-$C_4H_9$ | n-$C_4H_9$ | n-$C_4H_9$ |
| (22) | n-$C_5H_{11}$ | n-$C_5H_{11}$ | $CH_3$ | $CH_3$ |
| (23) | n-$C_5H_{11}$ | n-$C_5H_{11}$ | $C_2H_5$ | $C_2H_5$ |

-continued

| | | | | |
|---|---|---|---|---|
| (24) | n-C$_5$H$_{11}$ | n-C$_5$H$_{11}$ | n-C$_3$H$_7$ | n-C$_3$H$_7$ |
| (25) | n-C$_5$H$_{11}$ | n-C$_5$H$_{11}$ | n-C$_4$H$_9$ | n-C$_4$H$_9$ |

(26)–(45)

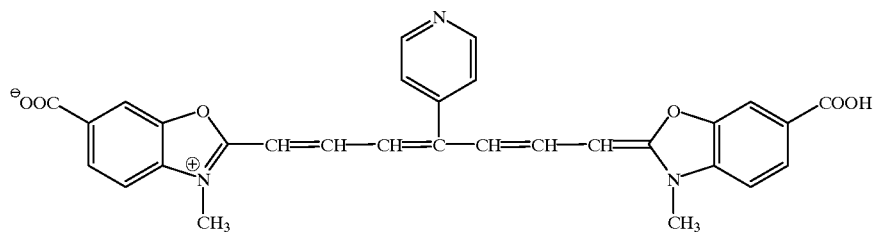

| No. | R$^{47}$ | R$^{48}$ | R$^{49}$ | R$^{50}$ |
|---|---|---|---|---|
| (26) | CH$_3$ | CH$_3$ | CH$_3$ | CH$_3$ |
| (27) | CH$_3$ | CH$_3$ | C$_2$H$_5$ | C$_2$H$_5$ |
| (28) | CH$_3$ | CH$_3$ | n-C$_3$H$_7$ | n-C$_3$H$_7$ |
| (29) | CH$_3$ | CH$_3$ | n-C$_4$H$_9$ | n-C$_4$H$_9$ |
| (30) | C$_2$H$_5$ | C$_2$H$_5$ | CH$_3$ | CH$_3$ |
| (31) | C$_2$H$_5$ | C$_2$H$_5$ | C$_2$H$_5$ | C$_2$H$_5$ |
| (32) | C$_2$H$_5$ | C$_2$H$_5$ | n-C$_3$H$_7$ | n-C$_3$H$_7$ |
| (33) | C$_2$H$_5$ | C$_2$H$_5$ | n-C$_4$H$_9$ | n-C$_4$H$_9$ |
| (34) | n-C$_3$H$_7$ | n-C$_3$H$_7$ | CH$_3$ | CH$_3$ |
| (35) | n-C$_3$H$_7$ | n-C$_3$H$_7$ | C$_2$H$_5$ | C$_2$H$_5$ |
| (36) | n-C$_3$H$_7$ | n-C$_3$H$_7$ | n-C$_3$H$_7$ | n-C$_3$H$_7$ |
| (37) | n-C$_3$H$_7$ | n-C$_3$H$_7$ | n-C$_4$H$_9$ | n-C$_4$H$_9$ |
| (38) | n-C$_4$H$_9$ | n-C$_4$H$_9$ | CH$_3$ | CH$_3$ |
| (39) | n-C$_4$H$_9$ | n-C$_4$H$_9$ | C$_2$H$_5$ | C$_2$H$_5$ |
| (40) | n-C$_4$H$_9$ | n-C$_4$H$_9$ | n-C$_3$H$_7$ | n-C$_3$H$_7$ |
| (41) | n-C$_4$H$_9$ | n-C$_4$H$_9$ | n-C$_4$H$_9$ | n-C$_4$H$_9$ |
| (42) | n-C$_5$H$_{11}$ | n-C$_5$H$_{11}$ | CH$_3$ | CH$_3$ |
| (43) | n-C$_5$H$_{11}$ | n-C$_5$H$_{11}$ | C$_2$H$_5$ | C$_2$H$_5$ |
| (44) | n-C$_5$H$_{11}$ | n-C$_5$H$_{11}$ | n-C$_3$H$_7$ | n-C$_3$H$_7$ |
| (45) | n-C$_5$H$_{11}$ | n-C$_5$H$_{11}$ | n-C$_4$H$_9$ | n-C$_4$H$_9$ |

(46)

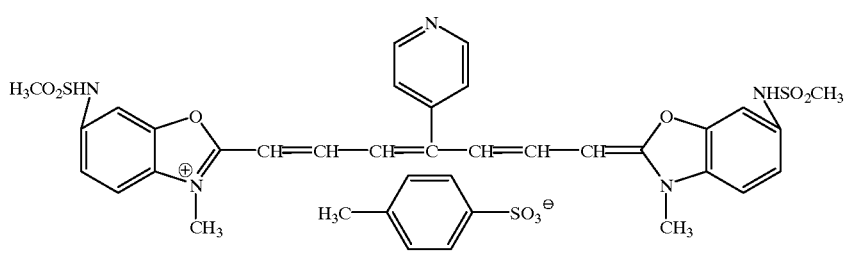

(47)

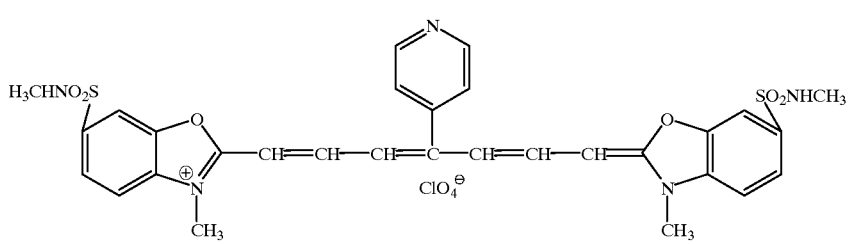

(48)

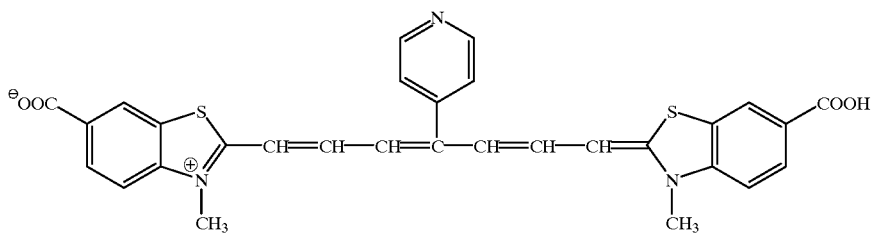
(49)
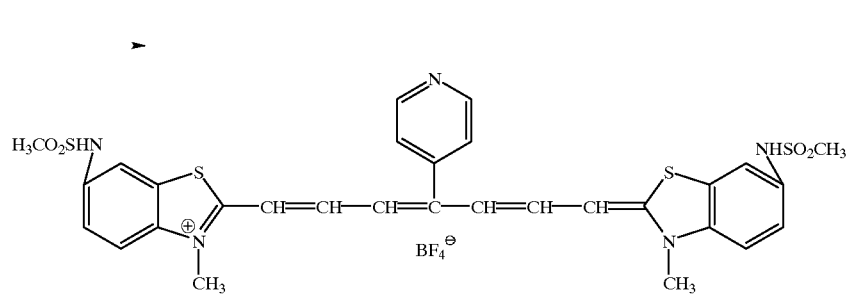
(50)
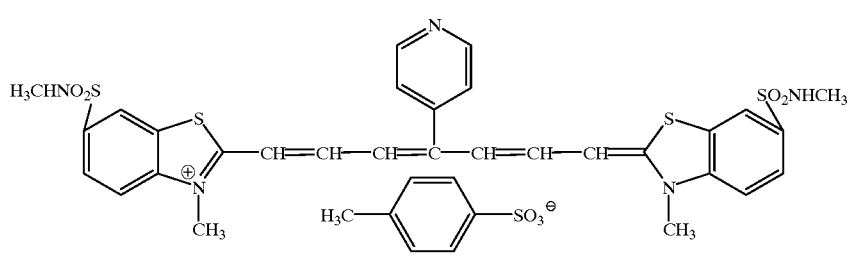
(51)
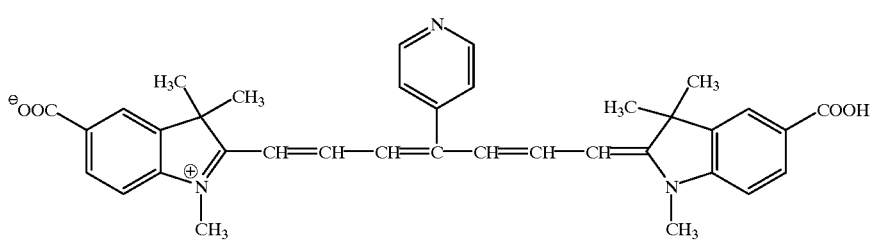
(52)
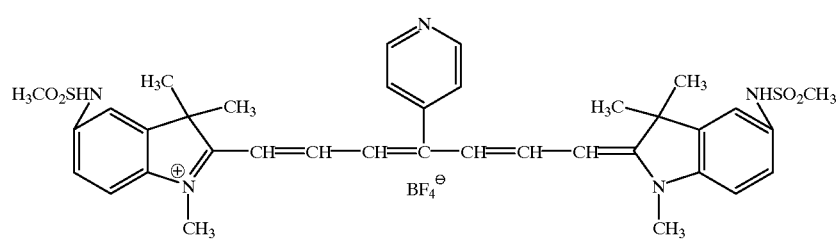
(53)
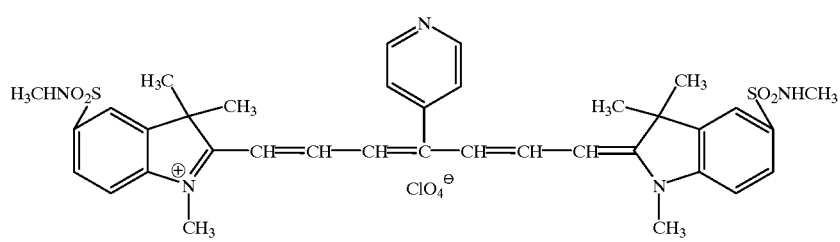
(54)

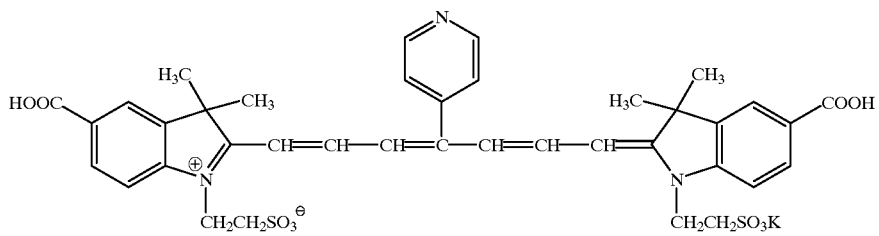
(55)
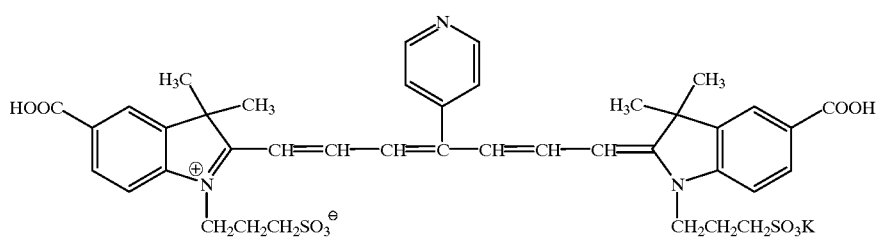
(56)
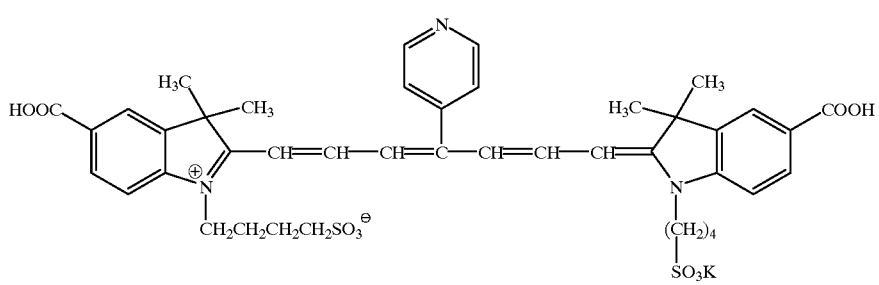
(57)
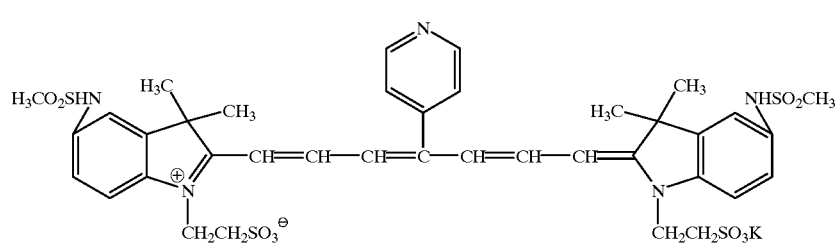
(58)
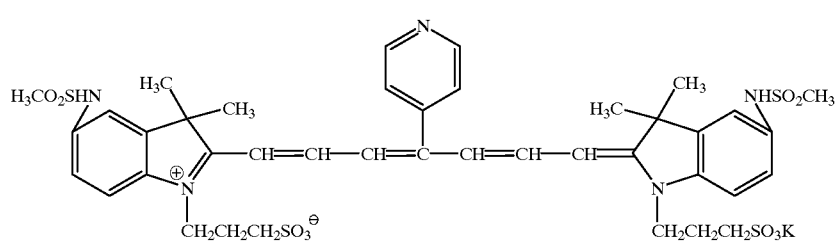
(59)
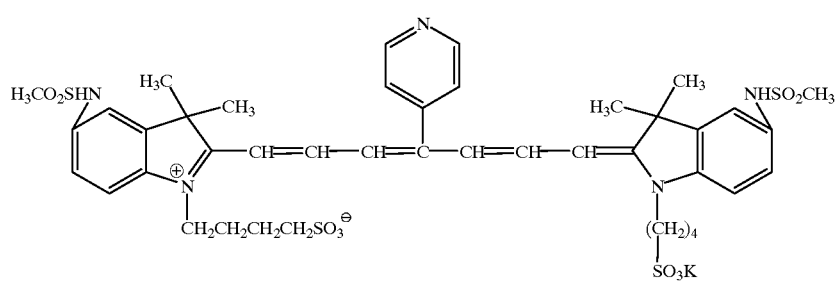
(60)

-continued

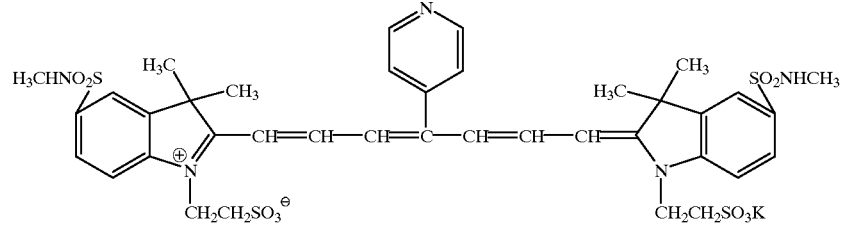
(61)

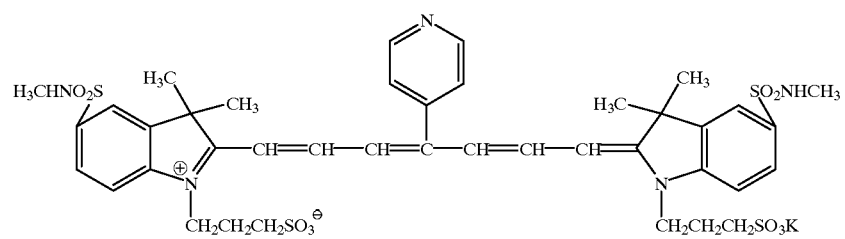
(62)

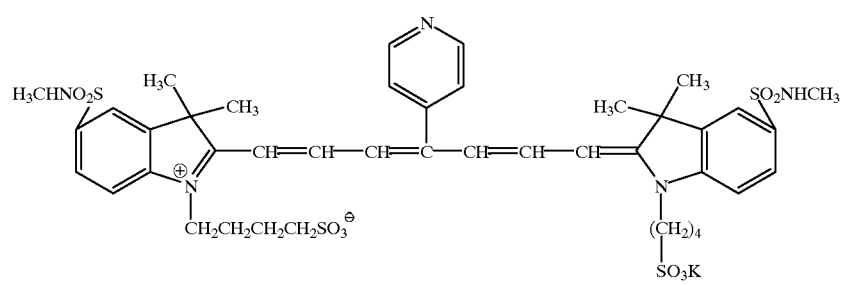
(63)

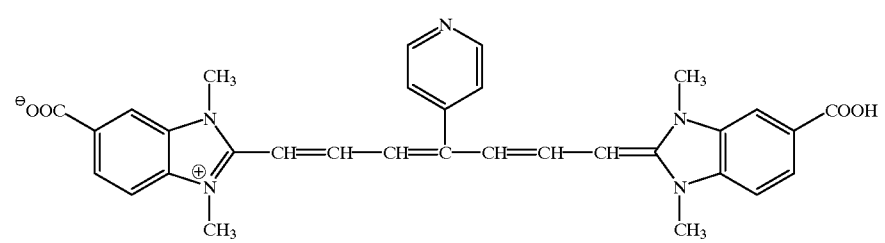
(64)

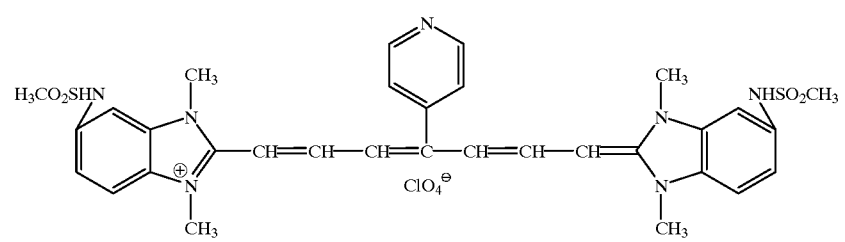
(65)

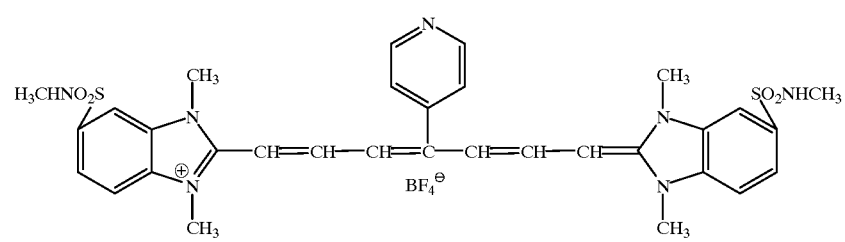
(66)

The chemical structure of the heptamethine cyanine compound of the present invention is characterized in that the meso-position of the heptamethine chain is substituted with 4-pyridyl. The heptamethine cyanine compound of the invention as a near infrared absorbing dye is characterized in that absorption within the visible region is very small. The compound of the present invention is preferably used in the form of a dispersion or a coated layer of the dispersion, rather than a solution or a coated layer of the solution, to reduce absorption within the visible region. In the dispersion, the dye is preferably in the form of J aggregates.

J aggregates of spectral sensitizing dyes used in silver halide photographic materials are described in H. T. James, The Theory of the Photographic Process, Macmillan Publishing Co., Inc., (1977), pages 218 to 222. The J aggregates of the spectral sensitizing dye are adsorbed on silver halide grains. The absorption maximum ($\lambda$max) of the adsorbed J aggregates is longer than that of the same dye contained in a solution. The J aggregates described in The Theory of the Photographic Process are formed on a carrier such as silver halide grains. Accordingly, the same J aggregates are scarcely formed without a carrier. Dyes other than spectral sensitizing dyes are usually used without a carrier.

A specific form of a dye other than the adsorbed dye described in The Theory of the Photographic Process, for example, a solid fine particle dispersion of a dye has the absorption maximum longer than that of the dye contained in a solution. The solid fine particle dispersion can be obtained by dispersing a dye mechanically (for example by using a sand grinder mill).

In the present specification, the term "J aggregates" means a specific form of a dye having the absorption maximum longer than the that of the dye contained in a solution.

The J aggregates can be prepared as is described below.

First, the J aggregates can be formed by precipitation caused by a pH change.

The heptamethine cyanine compound of the present invention is dissolved in an aqueous alkali (e.g., NaOH, KOH) solution, and is neutralized with an acid (e.g., hydrochloric acid, acetic acid, citric acid) to precipitate the J aggregates. An organic base having a function of dissolving the compound of the invention in water can be used in place of an alkali (inorganic base). The aqueous solution of the alkali or the organic base preferably has a pH about 12. The acid is merely required to neutralize the alkaline solution having a pH about 12. Accordingly, various inorganic or organic, monobasic or polybasic acids can be used.

The obtained precipitate contains so small size particles, which cannot be observed with an optical microscope. Ultra fine particles of about several tens Å are observed with a transparent electron microscope. It is difficult to determine such ultra fine particles dispersed in a solvent as a dispersion of solid fine particles or as aggregates in the form of a solution. In conclusion, the obtained liquid of the J aggregates is on the borderline between a dispersion and a solution.

The obtained aggregates are left to cause sedimentation. The aggregation can be condensed by natural sedimentation or centrifugation. A dispersing agent (e.g., anionic or nonionic surface active agents) is added to the obtained aggregates, and the mixture is stirred to disperse the aggregates again. Thus a J aggregates liquid is obtained. The mixture can be stirred by an ultrasonic waver, an impeller type stirring machine (e.g., dissolver), or a dispersing machine (e.g., sand grinder mill). The obtained J aggregates liquid has a $\lambda$max longer than the $\lambda$max of a methanol solution. The difference in the $\lambda$max is larger than 100 nm. The half-width of the spectrum is not larger than 120 nm, which means that the absorption spectrum of J aggregates is sharp.

Second, the J aggregates can be formed by a mechanical dispersing method.

If a dye is directly dispersed by a dispersing machine (e.g., sand grinder mill), the half-width would usually be wide and the absorption spectrum would usually be broad. However, J aggregates can be obtained by directly dispersing the heptamethine cyanine compound of the present invention. In other words, the mechanical dispersion of the heptamethine cyanine compound of the present invention shows a sharp absorption spectrum similar to the spectrum of the J aggregates formed by precipitation.

The fine particles obtained by the mechanical dispersing method have an average particle size preferably in the range of 0.005 to 10 $\mu$m, more preferably in the range of 0.01 to 1 $\mu$m, further preferably in the range of 0.01 to 0.5 $\mu$m, and most preferably in the range of 0.01 to 0.1 $\mu$m.

Third, the J aggregates can be formed by precipitation caused by addition of a bad solvent.

The heptamethine cyanine compound is dissolved in an organic solvent (e.g., methanol, dimethylformamide). A bad solvent is then added to the solution to obtain a dispersion of the J aggregates.

Fourth, the J aggregates can be formed by precipitation caused by addition of a polymer.

The fourth method is effective in the case that the heptamethine cyanine compound of the present invention has a high water solubility (for example, a compound substituted with sulfo). In more detail, an aqueous solution of the heptamethine cyanine compound is added to an aqueous solution of a polymer (e.g., gelatin) to precipitate the compound as J aggregates.

The J aggregates prepared by the above-mentioned methods does not cause any problems on the near infrared absorbing characteristics (e.g., absorption spectrum, fixation, removal) of the compound of the present invention.

Where the compound of the present invention is used in the form of J aggregates, absorption within the visible region is scarcely observed, which means that the absorption spectrum is an ideal of a near infrared absorbing dye. Further, the compound of the present invention is also excellent in fixation and removal.

The fixation of a dye means nondiffusion between a layer containing a dye and another layer. The fixation can be further improved by heating J aggregates of the compound of the present invention.

The J aggregates of the compound of the present invention scarcely have absorption within the visible region. In some case, the compound can remain after use of it because the compound is substantially invisible. Even in the case that the compound should be removed, the compound of the present invention can easily be dissolved in various processing solutions. Sulfite ion is preferably added to the processing solution. The sulfite ion has a function of accelerating dissolution of the compound and a function of reacting the compound to decolor the processing solution.

The heptamethine cyanine compound of the present invention can be used in an infrared absorbing ink. The compound of the present invention is dissolved in an organic solvent (e.g., methanol, dimethylformamide) or an aqueous alkali (e.g., NaOH, KOH) solution. The obtained solution can be used as the infrared absorbing ink. However, a dispersion (particularly a dispersion of J aggregates) has a small absorption within the visible region, compared with the solution. Accordingly, a dispersion of the compound is preferably used as the infrared absorbing ink. The dispersion can be prepared according to one of the above-mentioned four methods.

The near infrared absorbing ink can further contain a binder or a surface active agent.

The concentration of the heptamethine cyanine compound in the infrared absorbing ink is preferably in the range of 0.02 to 10 wt. %, more preferably in the range of 0.02 to 5 wt. %, and most preferably in the range of 0.02 to 3 wt. %.

A near infrared absorbing sheet can be prepared by coating the near infrared absorbing ink on a transparent support. A binder is preferably used in the preparation of the near infrared absorbing sheet. A hydrophilic polymer (e.g., gelatin) is preferably used as the binder. A hardening agent (e.g., 1,2-bis(sulfonylacetamido)ethane) can be used to harden the binder.

The coating amount of the heptamethine cyanine compound of the present invention in the infrared absorbing sheet is preferably in the range of 0.001 to 1 $g/m^2$, and more preferably in the range of 0.005 to 0.5 $g/m^2$.

The coating amount of the binder is preferably in the range of 0.01 to 100 $g/m^2$, and more preferably in the range of 0.1 to 20 $g/m^2$.

The material and the thickness of the support should be selected to make the support transparent to light within the visible region. The transparent support preferably is a plastic (e.g., polyethylene terephthalate) film or a glass plate.

The infrared absorbing sheet can be used as a filter of a plasma display panel (PDP). The plasma display panel emits an infrared ray, which disturbs a remote controller. The infrared absorbing sheet is attached to the surface of the panel to shield the infrared ray emitted from the display.

The heptamethine cyanine compound can also be used as an infrared absorbing dye in a silver halide photographic material. The heptamethine cyanine compound of the present invention is characterized in that absorption with in the visible region is small. Further, the compound can be fixed in a specific layer. Furthermore, it is easy to remove the compound from the photographic material. Therefore, the compound is advantageously used as an infrared absorbing dye in a silver halide photographic material.

In the case that a silver halide photographic material is usually treated in an automatic developing machine having an infrared detecting mechanism, a near infrared absorbing dye is added to a photographic material to improve precision in detection of the material. It is rather difficult to detect a photographic material containing a relatively small coating amount (1 to 5 $g/m^2$) of silver halide. Examples of the photographic material containing the small amount of silver halide include a black and white photographic material, an X ray sensitive photographic material and an infrared sensitive photographic material. Particularly, an X ray sensitive black and white photographic material for a medical use contains a very small coating amount (1.5 to 4 $g/m^2$) of silver halide, though the photographic material has two silver halide emulsion layers provided on each side of a support. The heptamethine cyanine compound is particularly effective in the silver halide photographic material containing a small coating amount of silver halide.

The heptamethine cyanine compound of the present invention can also be used as a filter dye, an antihalation dye or an antiirradiation dye of a near infrared sensitive silver halide photographic material.

Even though the heptamethine cyanine compound is not completely removed from a photographic material after forming an image, the remaining compound does not disturb the formed image because the compound has little absorption within the visible region. Further, it is easy to remove the compound from the photographic material. A photographic processing solution usually has a function of removing a dye from a photographic material as well as a main function of processing an image forming reaction. A silver halide photographic material containing the compound of the invention as a dye, the processing solution does not require the function of removing the dye. Accordingly, the photographic material containing the compound of the present invention has an effect that the amount of the processing solution (particularly replenisher) can be reduced.

A silver halide photographic material comprises a support, at least one silver halide emulsion layer and at least one non-light-sensitive hydrophilic colloidal layer. The heptamethine cyanine compound of the present invention is added to the silver halide emulsion layer or the non-light-sensitive hydrophilic colloidal layer. A photographic dye is usually added to the non-light-sensitive hydrophilic colloidal layer, except that an antiirradiation dye is added to the silver halide emulsion layer.

The compound of the present invention is preferably used in the form of a dispersion (particularly a dispersion of J aggregates) rather than a solution to reduce absorption within the visible region.

The coating amount of the heptamethine cyanine compound in the silver halide photographic material is preferably in the range of 0.001 to 1 $g/m^2$, and more preferably in the range of 0.005 to 0.5 $g/m^2$.

A hydrophilic colloid of the non-light-sensitive layer or a protective colloid of the silver halide emulsion layer (usually gelatin) can function as a binder of the compound of the present invention.

A silver halide photographic material is described in various document. The heptamethine cyanine compound can be used in various silver halide photographic material. As is described above, the compound is particularly effective in an X-ray sensitive photographic material or a near infrared ray sensitive photographic material.

An automatic developing machine having an infrared detecting mechanism (an infrared sensor) is commercially available. The infrared sensor comprises an infrared (700 nm or more) light source, such as a light emitting diode, a semiconductor laser, and a light receiving element having a sensitivity within the region of 700 to 1,200 nm.

Synthesis Example 1

Synthesis of Compound (1)

In a reaction vessel, 2.2 g of the following compound (a), 1.0 g of the following compound (b) and 25 ml of methanol were placed. The mixture was stirred at room temperature. To the mixture, 2 ml of triethylamine was added. The mixture was further stirred at room temperature for 2 hours. After 2 hours, 1 ml of acetic anhydride was gradually added to the mixture. The reaction was continued at room temperature for 3 hours. The precipitates were filtered off, washed with methanol, and dried to obtain 0.7 g of the compound (1). The chemical structure of the compound was confirmed with NMR and MS.

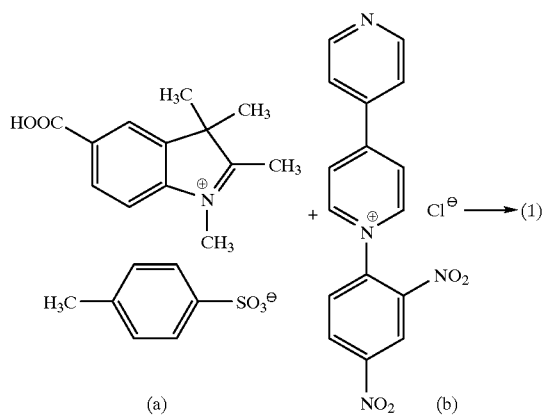

Synthesis Example 2
Synthesis of Compound (6)

In a reaction vessel, 4.4 g of the following compound (c), 1.8 g of the following compound (d) and 50 ml of methanol were placed. The mixture was stirred at room temperature. To the mixture, 2.1 ml of triethylamine was added. The mixture was left at room temperature over one night. Precipitates were filtered off, washed with methanol, and dried to obtain 0.6 g of the compound (6). The chemical structure of the compound was confirmed with NMR and MS.

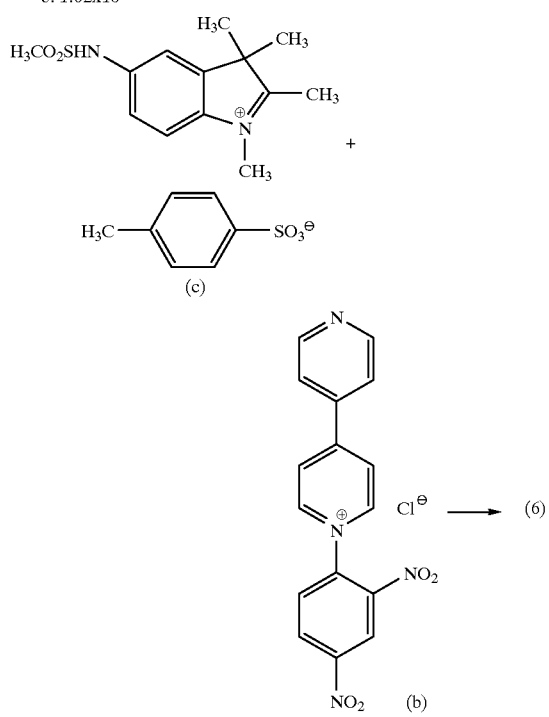

Synthesis Example 3
Synthesis of Compound (56)

In a reaction vessel, 3.3 g of the following compound (d), 1.8 g of the following compound (b) and 20 ml of methanol were placed. The mixture was stirred at room temperature. To the mixture, 2.1 ml of triethylamine was added. The mixture was stirred at room temperature for 4 hours. Since the reaction was not completed, 0.5 g of the compound (d) was further added to the mixture. The reaction was continued at 50° C. for 2 hours. After cooling the mixture, a solution of 1.0 g of potassium acetate in 5 ml of methanol was gradually added to the mixture to precipitate a compound. Precipitates were filtered off, washed with methanol, and dried to obtain 2.1 g of the compound (56). The chemical structure of the compound was confirmed with NMR and MS.

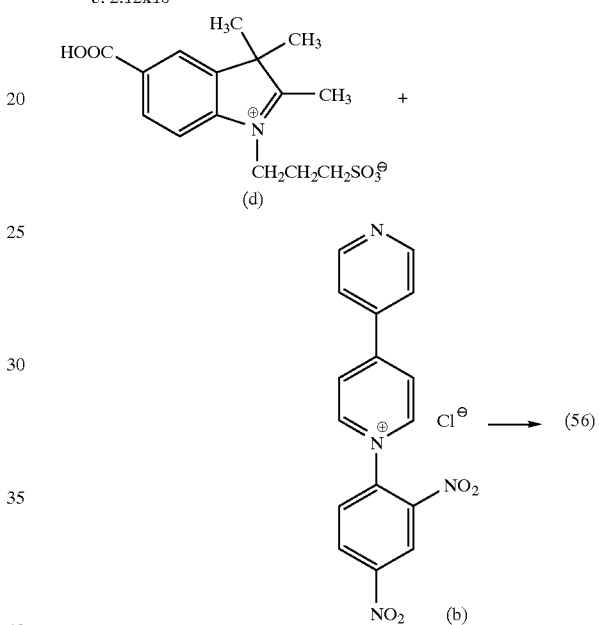

EXAMPLE 1
Preparation of Near Infrared Absorbing Ink (pH Change Precipitating Method)

In a beaker, 100 mg of the compound (1) was placed. To the compound, 450 ml of distilled water was added. Further, 30 ml of 1 N aqueous solution of sodium hydroxide was added to the mixture. The resulting mixture was stirred by a magnetic stirrer. After confirming that the compound was completely dissolved, acetic acid was dropwise added to the solution to adjust the pH in the range of 5 to 7. As a result, very fine particles were precipitated. Separately, 2.1 g of 25 wt. % aqueous solution of a surface active agent (Demol EP, Kao Co., Ltd.) was diluted with distilled water to 100 ml. To the dispersion of the fine particles, 20 ml of the diluted surface active agent solution was added to obtain 500 ml of a near infrared absorbing ink (a dye dispersion). The concentration of the dye was 0.02 wt. %.

The solid content of the obtained near infrared absorbing ink was adjusted to 5 wt. %. The same solid content (wt. %) of photographic gelatin was added to the ink. Further, an aqueous solution of the following antiseptic was added to the ink. The amount of the antiseptic to gelatin was 2,000 ppm. The ink was cooled, and stored in a form like a jelly.

Antiseptic

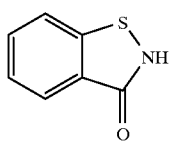

EXAMPLE 2
Preparation of Near Infrared Absorbing Ink (pH Change Precipitating, Aggregating and Dispersing Method)

An aqueous alkali solution of the compound (1) was prepared in the same manner as in Example 1. Acetic acid was dropwise added to the solution to neutralize the alkali, and the resulting solution was left for several hours. As a result, fine precipitates were aggregated to cause sedimentation. After the solution was left over one night, a supernatant was decanted to obtain 180 ml of an aggregate liquid. To the liquid, 20 ml of the diluted surface active agent solution used in Example 1 was added to obtain 200 ml of a near infrared absorbing ink (a dye dispersion). The concentration of the dye was 0.05 wt. %.

The obtained near infrared absorbing ink was treated and stored in the same manner as in Example 1.

EXAMPLE 3
Preparation of Near Infrared Absorbing Ink (Mechanical Dispersing Method)

The compound (1) was treated as a wet cake without drying it, and 6.3 g of the compound (1) was weighed as the dry solid content. To the compound, 10 wt. % aqueous solution of a surface active agent (Demol EP, Kao Co., Ltd.) was added. The dry solid content of the surface active agent was 30 wt. % of the dry solid content of the compound (1). Water was added to the mixture to give a total amount of 63.3 g. The mixture was well stirred to obtain slurry. The slurry and 100 cc of zirconia beads (average diameter: 0.5 mm) were placed in a vessel. The contents of the vessel were dispersed in a dispersing machine (1/16 G sand grinder mill, Aimex Co., Ltd.) for 6 hours. Water was added to the mixture to obtain a near infrared absorbing ink (dye dispersion). The concentration of the dye was 8 wt. %.

The obtained near infrared absorbing ink was treated and stored in the same manner as in Example 1.

EXAMPLE 4
Preparation of Near Infrared Absorbing Ink (Mechanical Dispersing Method)

A near infrared absorbing ink (dye dispersion) was prepared in the same manner as in Example 3, except that the same amount of the compound (6) was used in place of the compound (1).

The obtained near infrared absorbing ink was treated and stored in the same manner as in Example 1.

EXAMPLE 5
Preparation of Near Infrared Absorbing Ink (Mechanical Dispersing Method)

A near infrared absorbing ink (dye dispersion) was prepared in the same manner as in Example 3, except that the same amount of the compound (14) was used in place of the compound (1).

The obtained near infrared absorbing ink was treated and stored in the same manner as in Example 1.

Comparison Example 1
Preparation of Near Infrared Absorbing Ink (Mechanical Dispersing Method)

A near infrared absorbing ink (dye dispersion) was prepared in the same manner as in Example 3, except that the same amount of the following comparative compound (x) was used in place of the compound (1).

The obtained near infrared absorbing ink was treated and stored in the same manner as in Example 1.

Comparative Compound (x)

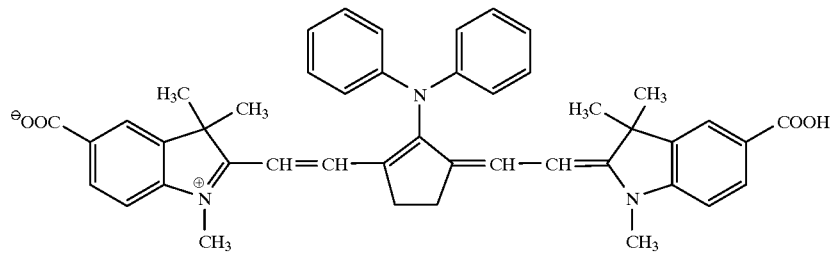

Comparison Example 2

Preparation of Near Infrared Absorbing Ink (Mechanical Dispersing Method)

A near infrared absorbing ink (dye dispersion) was prepared in the same manner as in Example 3, except that the same amount of the following comparative compound (y) was used in place of the compound (1).

The obtained near infrared absorbing ink was treated and stored in the same manner as in Example 1.

Comparative Compound (y)

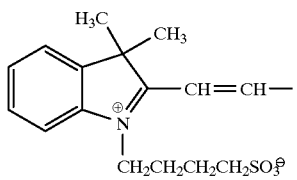 

EXAMPLE 6
Preparation of Near Infrared Absorbing Ink (Polymer Precipitating Method)

In a beaker, 100 mg of the compound (56) was placed. To the compound, 250 ml of distilled water was added. The mixture was stirred with a magnetic stirrer to dissolve the compound in water completely.

The obtained solution was added to 250 ml of 10 wt. % aqueous solution of gelatin. The compound was very finely precipitated. The fine particles were not observed with eyes, since gelatin functioned as a dispersing agent. Thus, a near infrared absorbing ink (dye dispersion) was prepared.

EXAMPLE 11
Preparation of Near Infrared Absorbing Sheet

The following hardening agent was added to the near infrared absorbing ink prepared in Example 1. The obtained mixture was coated on a gelatin undercoating layer formed on a polyethylene terephthalate film to prepare a near infrared absorbing sheet. The coating amounts of the additives are shown below.

| Additives | Coating amount |
|---|---|
| Gelatin | 4.2 g/m² |
| Near infrared absorbing dye (Compound (1)) | 10 mg/m² |
| Hardening agent (1,2-bis(sulfonyladetamido)ethane) | 125 mg/m² |

EXAMPLES 12 to 16

Comparison Examples 11 and 12
Preparation of Near Infrared Absorbing Sheets

Near infrared absorbing sheets were prepared in the same manner as in Example 11, except that the near infrared absorbing inks prepared in Examples 2 to 6, Comparison Examples 11 and 12 were used respectively.

Evaluation of Absorption Spectrum

Absorption spectra of the near infrared absorbing sheets prepared in Examples 11 (pH change precipitating method) and 13 (mechanical dispersing method) were measured. The results are shown in FIG. 1.

Further, absorption spectrum of the near infrared absorbing sheet prepared in Example 16 (polymer precipitating method) was measured. The results are shown in FIG. 2.

Furthermore, absorption spectrum of the near infrared absorbing sheet prepared in Comparison Example 11 (using the comparative compound (x)) was measured. The results of the Comparison Example 11 were compared with the results of Example 1 (using the compound (1)), as is shown in FIG. 3.

Figure 2:
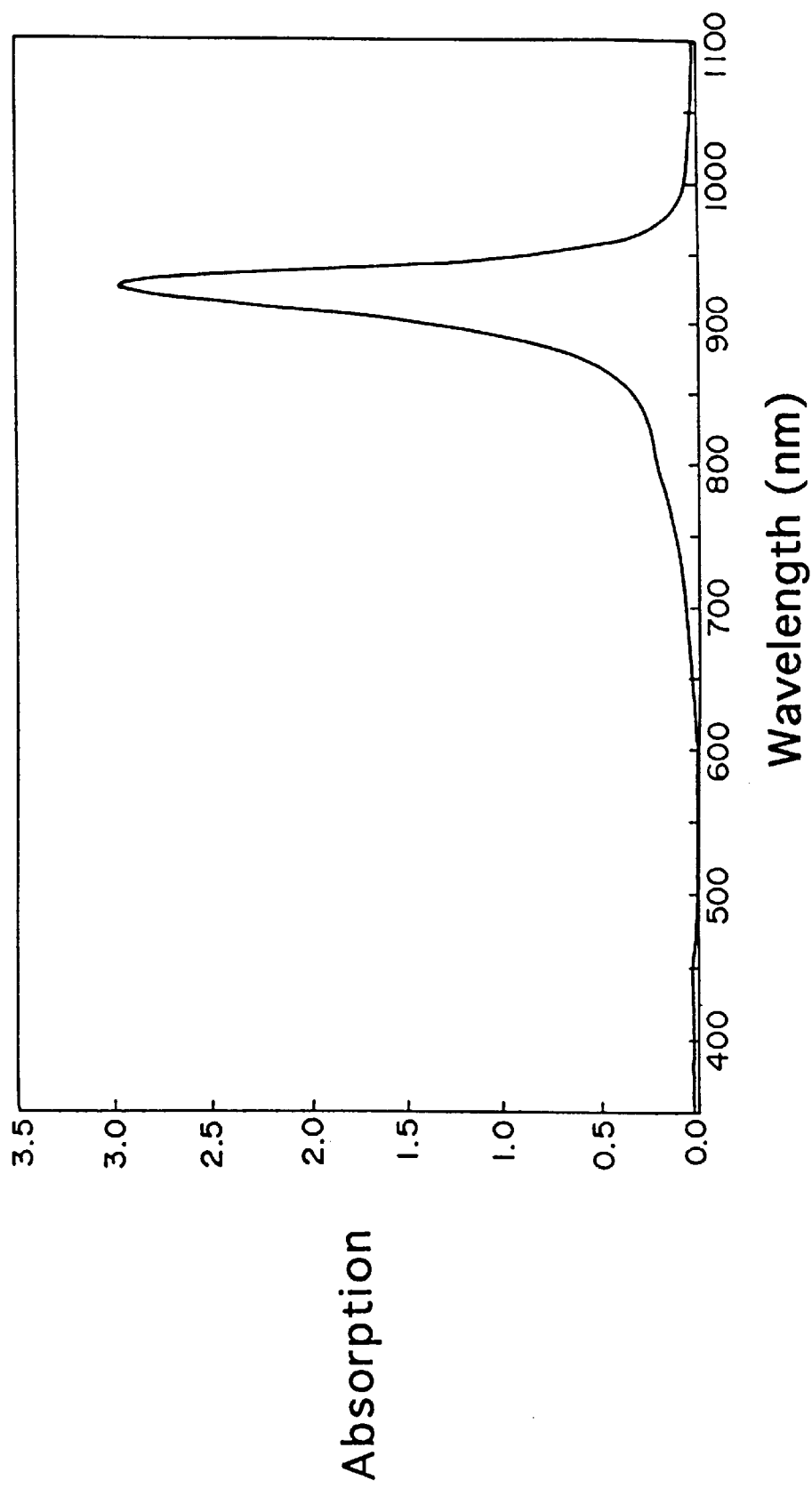
FIG. 2 is a graph showing absorption spectrum of a near infrared absorbing sheet prepared in Example 16.
Figure 3:
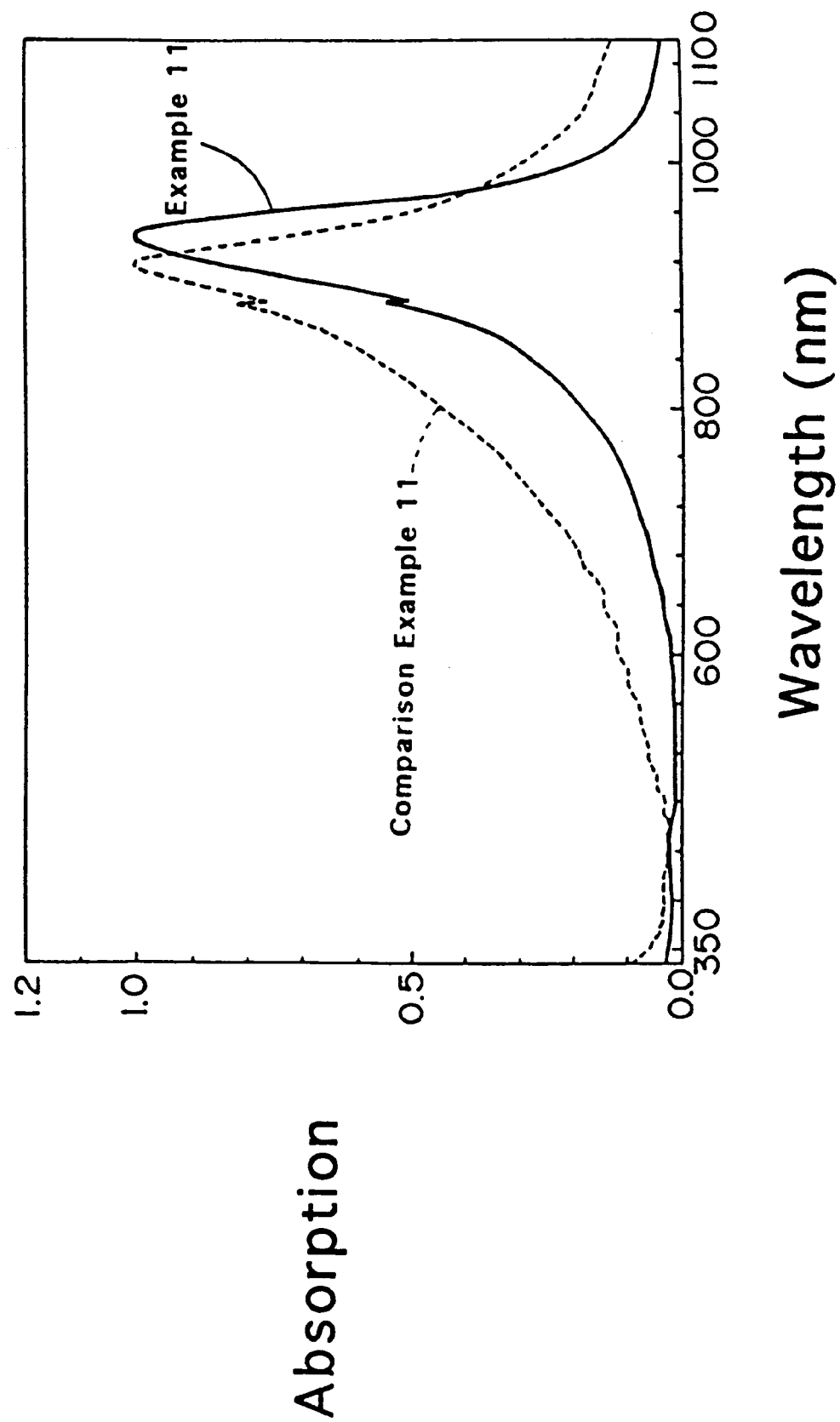
FIG. 3 is a graph showing absorption spectra of near infrared absorbing sheets prepared in Comparison Example 11 and Example 1.

As is evident from the absorption spectra shown in FIGS. 1 to 3, the near infrared absorbing sheets using the compound of the present invention has little absorption within the visible region and a sharp absorption peak within the near infrared region.

Evaluation of Fixation

The near infrared absorbing sheets prepared in Examples 13 (using the compound (1), 14 (using the compound (6)), 15 (using the compound (14)), Comparison Example 11 (using the comparative compound (x)) and 12 (using the comparative compound (y)) were immersed in a distilled water at 35° C. for 5 minutes, and dried. Before and after the above-mentioned treatment, the optical density at λmax was measured. The fixation of the dye was evaluated as the remaining ratio of the optical density.

The results are set forth in Table 1.

Evaluation of Decoloring Characteristic

To a buffer solution containing 0.1 M of sodium caronate and 0.2 M of sodium hydrogen carbonate (pH: 10) sodium sulfite (10 g per liter) was added to prepared a processing solution.

The near infrared absorbing sheets prepared in Examples 13, 14, 15, Comparison Examples 11 and 12 were immersed in the processing solution at 35° C. for 45 seconds, and dried. Before and after the above-mentioned treatment, the optical density at λmax was measured. The decoloring characteristic of the dye was evaluated as the remaining ratio of the optical density.

The results are set forth in Table 1.

TABLE 1

| Sheet | Dye | Fixation | Decoloring | λmax |
|---|---|---|---|---|
| Example 13 | (1) | 96% | 0% | 950 nm |
| Example 14 | (6) | 100% | 0% | 1,007 nm |
| Example 15 | (14) | 98% | 0% | 1,005 nm |
| Comp. 11 | (x) | 99% | 97% | 930 nm |
| Comp. 12 | (y) | 0% | 0% | 765 nm |

As is evident from the results shown in Table 1, the compounds of the present invention have a high fixing ratio because the compounds are scarcely dissolved in distilled water. However, the compounds of the present invention can easily be dissolved in a processing solution containing sulfite ion.

Evaluation of Near Infrared Absorption

Each of ten near infrared absorbing sheets prepared in Example 11 (optical density at 930 nm: 0.6 or more) was inserted into inlet of an automatic developing machine (remodeled FPM-9000, Fuji Photo Film Co., Ltd.). Number of the detected sheets was counted. The automatic developing machine has a pair of an infrared emitting element (GL-514, Sharp Corporation) and a light receiving element (PT501B, Sharp Corporation) at the film inlet. When the emitted infrared ray is shielded by an inserted film, a conveying roller starts to convey the film to a developing tank automatically.

When each of the ten near infrared absorbing sheets prepared in Example 11 was inserted into the inlet of the developing machine, the conveying roller started. Therefore, the infrared absorption of the sheet was confirmed.

Independently, each of ten polyethylene terephthalate films (used in preparation of the infrared absorbing sheet) was inserted into the inlet of the automatic developing machine. As a result, the conveying roller did not start at all.

EXAMPLES 21 to 23

Comparison Examples 21 and 12

Preparation of Dispersions of Near Infrared Absorbing Dye

Each of the compounds (1), (6), (14) and the comparative compound (x) was treated as a wet cake without drying it. To 2.5 g (dry solid content) of the compound, 3 g of 25 wt. % aqueous solution of a surface active agent (Demol EP, Kao Co., Ltd.) was added. Water was added to the mixture to give a total amount of 63.3 g. The mixture was well stirred to obtain slurry. The slurry and 100 cc of zirconia beads (diameter: 0.8 to 1.2 mm) were placed in a vessel. The contents of the vessel were dispersed in a dispersing machine (1/16G sand grinder mill, Aimex Co., Ltd.) for 12 hours. Water was added to the mixture to obtain a dispersion of a near infrared absorbing dye. The concentration of the dye was 2 wt. %.

Preparation of Silver Halide Emulsion

In 820 cc of water, 3 g of sodium chloride, gelatin (average molecular weight: 20,000) and 0.04 g of 4-aminopyrazolo [3,4-d]pyrimidine were dissolved. To the solution kept at 55° C., an aqueous solution of 10.0 g of silver nitrate and an aqueous solution of 5.61 g of potassium bromide and 0.72 g of potassium chloride were added according to a double jet method for 30 seconds while stirring. To the mixture, an aqueous solution of 20 g of acid treated gelatin (prepared by treating alkali treated gelatin with hydrogen peroxide) and 6 g of potassium chloride was added. The mixture was left for 25 minutes. to the mixture, an aqueous solution of 155 g of silver nitrate and an aqueous solution of 87.3 g of potassium bromide and 21.9 g of potassium chloride were added according to a double jet method for 58 minutes. The flow rate of the double jet method was so accelerated that the final flow rate was three times as fast as the first flow rate.

To the resulting mixture, an aqueous solution of 5 g of silver nitrate and an aqueous solution of 2.7 g of potassium bromide, 0.6 g of sodium chloride and 0.013 g of potassium ferrocyanide were added according to a double jet method for 3 minutes. The obtained emulsion was cooled to 350° C. to remove soluble salts according to a sedimentation method. The emulsion was heated to 400° C. To the emulsion, 28 g of gelatin, 0.4 g of zinc nitrate and 0.051 g of benzoisothiazolone were added. The emulsion was adjusted to pH 6.0 by using sodium hydroxide. Not less than 80% (base on projected area of grains) of the formed silver halide grains were tabular grains having an aspect ratio of not smaller than 3. The average diameter (based on the projected area) was 0.85 µm, the average thickness was 0.051 µm, and the chloride content was 20 mole %.

After the emulsion was heated to 56° C., 0.002 mole (based on silver) of silver iodide fine grains (average grain size: 0.05 µm) was added to the emulsion while stirring. To the emulsion, 4.8 mg of sodium ethylthiosulfonate, 500 mg of the following spectral sensitizing dye and 115 mg of 4-hydroxy-6-methyl-1,3,3a,7-tetrazaindene were added. To the emulsion, 1.8 g of chloroauric acid, 100 mg of potassium thiocyanate, 1.8 mg of sodium thiosulfate and 2.15 mg of the following selenium compound were added. The emulsion was subjected to chemical sensitization for 50 minutes, and cooled immediately to prepare a silver halide emulsion.

Spectral Sensitizing Dye

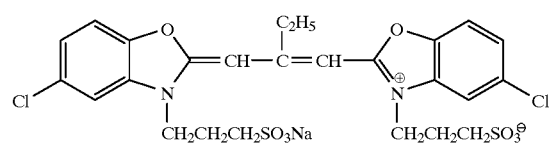

Selenium Compound

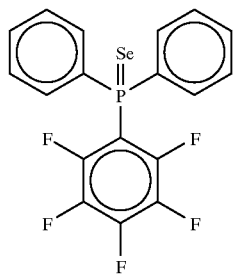

Preparation of Silver Halide Photographic Material

On each side of a polyethylene terephthalate film (thickness: 180 µm) colored with blue, a gelatin undercoating layer was formed. On each of the gelatin undercoating layers, a near infrared absorbing layer, a silver halide emulsion layer and a surface protective layer to prepare a silver halide photographic material (Examples 21 to 23, Comparison Examples 21 and 22). Examples 21 to 23 and Comparison Example 21 used the dispersions of the near infrared absorbing dyes (1), (6), (14) and (x) respectively. Comparison Example 22 did not use an infrared absorbing dye.

The compositions of the layers (coating amount on one side) are shown below.

| Near infrared absorbing layer | |
|---|---|
| Gelatin | 0.25 g/m² |
| Dispersion of a near infrared absorbing dye (solid content of dye) | 35 mg/m² |
| Sodium polyacrylate | 10 mg/m² |
| The following additive (1) | 2 mg/m² |
| The following additive (2) | 0.3 mg/m² |
| The following additive (3) | 4 mg/m² |

Additive (1)

[Structure: 1-phenyl-5-mercaptotetrazole sodium salt with COONa substituent on phenyl]

Additive (2)

[Structure: 1,3,4-thiadiazole with HS– and –S(CH₂)₄SO₃Na substituents]

Additive (3)

[Structure: 1-phenyl-5-mercaptotetrazole with SO₃Na on phenyl]

Silver halide emulsion layer

| | |
|---|---|
| 2,4-Bis(hydroxyamino)-4-diemthylamino-1,3,5-triazine | 3 mg/m² |
| Dextran (average molecular weight: 60,000) | 0.47 mg/m² |
| Sodium polystyrenesulfonate | 30 mg/m² |
| The following additive (A) | 115 mg/m² |
| The following additive (B) | 5 mg/m² |
| Gelatin | 1.0 g/m² |
| Silver halide emulsion (based on amount of coated silver) | 1.20 g/m² |
| 1,2-Bis(vinylsulfonylacetamido)ethane (hardening agent) | 43 mg/m² |

Additive (A)

[Structure: 1,4-dihydroxybenzene with SO₃Na substituent]

Additive (B)

[Structure: 5,6-dichloro-1,3-diethyl-benzimidazol-2-ylidene with =CH—CH=N—phenyl group]

Surface protective layer

| | |
|---|---|
| Gelatin | 0.55 g/m² |
| Matting agent | 0.10 g/m² |
| The following coating aid (1) | 22 mg/m² |
| The following coating aid (2) | 35 mg/m² |
| The following coating aid (3) | 5 mg/m² |
| The following coating aid (4) | 1 mg/m² |
| Sodium polyacrylate | 25 mg/m² |

Coating aid (1)

$C_8H_{17}$—(phenyl)—$(OCH_2CH_2)_3$—$SO_3Na$

Coating aid (2)
$C_{18}H_{33}O$—$(CH_2CH_2O)_{10}$—H

Coating aid (3)
$C_8F_{17}SO_3K$

Coating aid (4)
$C_8F_{17}SO_2N(C_3H_7)$—$(CH_2CH_2O)_4$—$(CH_2)_4$—$SO_3Na$ Preparation of Condensed Developing Solution
A condensed developing solution of the following composition was prepared.

| Condensed developing solution | |
|---|---|
| Diethylenetriaminepentaacetic acid | 8.0 g |
| Sodium sulfite | 10.0 g |
| Sodium carbonate monohydrate | 50.0 g |
| Potassium carbonate | 56.0 g |
| Sodium erythrobate (developing agent) | 60.0 g |
| 4-Hydroxymethyl-4-methyl-1-phenyl-3-pyrazolidone | 13.2 g |
| 3,3'-Diphenyl-3,3'-dithiopropionic acid | 1.44 g |
| 2,5-Dimercarpto-1,3,4-thiadiazole | 0.15 g |
| 2-(1,2-Dicarboxylethyl)thio-5-mercapto-1,3,4-thiadiazole | 0.40 g |
| Diethylene glycol | 50.0 g |
| Water (to make up to) | 1 liter |
| pH (adjusted with sodium hydroxide) | 10.5 |

Preparation of Developing Replenisher
The condensed developing solution was diluted twice to prepare a developing replenisher.
Preparation of Developing Mother Liquid
With water, 2 liters of the condensed developing solution was diluted twice to obtain 4 liters of a diluted developing solution. To the diluted developing solution, the following starter solution was added (60 ml based on 1 liter of the diluted developing solution) to prepare a developing mother liquid (pH: 9.6).

| Starter solution | |
|---|---|
| Potassium bromide | 11.1 g |
| Acetic acid | 10.8 g |
| Water (to make up to) | 60 ml |

Preparation of Condensed Fixing Solution
A condensed of fixing solution of the following composition was prepared.

| Condensed fixing solution | |
|---|---|
| Water | 500 ml |
| Ethylenediaminetetraacetic acid dihydrate | 0.05 g |
| Sodium thiosulfate tetrahydrate | 400 g |
| Sodium bisulfite | 200 g |
| 49 Wt. % aoueous solution of sodium hydroxide | 2.9 g |
| pH (adjusted with sodium hydroxide) | 5.2 |
| Water (to make up to) | 1 liter |

Preparation of Fixing Replenisher

The condensed fixing solution was diluted twice to prepare a developing replenisher.

Preparation of Fixing Mother Liquid

With water, 2 liters of the condensed fixing solution was diluted twice to obtain 4 liters of a developing mother liquid (pH: 5.4).

Process of Silver Halide Photographic Material

The silver halide photographic material was treated in an automatic developing machine (FPM-9000 remodeled to adjust the open ratio of 0.02, Fuji Photo Film Co., Ltd.) with the above-prepared developing and fixing mother liquids. Each of the developing and fixing replenishers was supplied to the mother liquid in an amount of 103 ml based on 1 m² of the photographic material. The processing conditions are shown below.

| Step | Temperature | Time |
| --- | --- | --- |
| Developing | 35° C. | 25 seconds |
| Fixing | 35° C. | 25 seconds |
| Washing | 25° C. | 22 seconds |
| Drying | 55° C. | 40 seconds |
| Total processing time (Dry to Dry) | | 120 seconds |

Evaluation of Sensor Detection

Each of ten sheets of the silver halide photographic material was inserted into the automatic developing machine. Number of the detected sheets was counted. The automatic developing machine has a pair of an infrared emitting element (GL-514, Sharp Corporation) and a light receiving element (PT501B, Sharp Corporation) at the film inlet. When the emitted infrared ray is shielded by an inserted film, a conveying roller starts to convey the film to a developing tank automatically. The results are set forth in Table 2.

Evaluation of Coloring of Processing Solution

After 100 sheets (size: 10×12 inch) of the silver halide photographic material were processed in the automatic developing machine, the color of the developing solution was evaluated with eyes. The results are set forth in Table 2. In Table 2, the grade A means that no color was observed in the developing solution, and the grade B means that the developing solution was gradually colored.

Evaluation of Sensitivity of Photographic Material

The silver halide photographic material was inserted between two screens (HR-4 screen, Fuji Photo Film Co., Ltd.). The photographic material was exposed to X ray through 10 cm of water-phantom. The photographic material was developed in the automatic developing machine to form an image. The sensitivity was measured as a relative value where the sensitivity of the sample of Example 21 is 100 based on the sum of 1.0 and the fogging value (including the density of the support). The results are set forth in Table 2.

Evaluation of Remaining Color After Process

After 100 sheets (size: 10×12 inch) of the silver halide photographic material were processed in the automatic developing machine, the remaining color within the unexposed area of the final sheet was evaluated with eyes. The results are set forth in Table 2. In Table 2, the grade A means that no remaining color was observed in the image, and the grade B means that the remaining color was remarkable in the image.

TABLE 2

| Photographic material | Infrared absorbing dye | Sensor detection | Coloring of solution | Sensitivity | Remaining color |
| --- | --- | --- | --- | --- | --- |
| Ex. 21 | (1) | 10/10 | A | 100 | A |
| Ex. 22 | (6) | 10/10 | A | 98 | A |
| Ex. 23 | (14) | 10/10 | A | 100 | A |
| Comp. 21 | (x) | 10/10 | B | 70 | B |
| Comp. 22 | None | 0/10 | A | 100 | A |

As is evident from the results shown in Table 2, the silver halide photographic materials using the compounds of the present invention as near infrared absorbing dyes can easily be detected with an infrared sensor. Further, the photographic materials have a high sensitivity. Furthermore, the photographic materials scarcely color processing solutions. Moreover, the compounds of the present invention do not remain in the formed image. A recent photographic process requires a small replenishing amount and a rapid development process. The photographic material using the compounds of the invention can satisfy the requirements.

As is described above, the heptamethine cyanine compound of the present invention has little absorption within the visible region. Accordingly, the compound can be used as an excellent (substantially ideal) near infrared absorbing dye. Therefore, the compound can advantageously be used in various materials such as a near infrared absorbing ink, a near infrared absorbing sheet or a silver halide photographic material.

We claim:

1. A heptamethine cyanine compound represented by the formula (I):

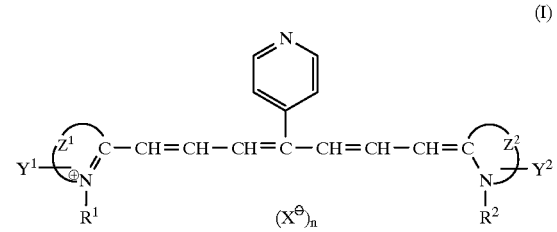

in which each of $Z^1$ and $Z^2$ independently is an atomic group that forms a five or six-membered heterocyclic ring or a five or six-membered heterocyclic ring condensed with benzene ring or naphthalene ring; each of $R^1$ and $R^2$ independently is an alkyl group having 1 to 20 carbon atoms or a substituted alkyl group having 1 to 20 carbon atoms; each of $Y^1$ and $Y^2$ independently is a substituent group which is selected from the group consisting of carboxyl, a sulfonamido group having 1 to 20 carbon atoms and a sulfamoyl group having 0 to 20 carbon atoms; X is an anion; and n is 0 or 1.

2. The heptamethine cyanine compound as defined in claim 1, wherein the compound is represented by the formula (IIa):

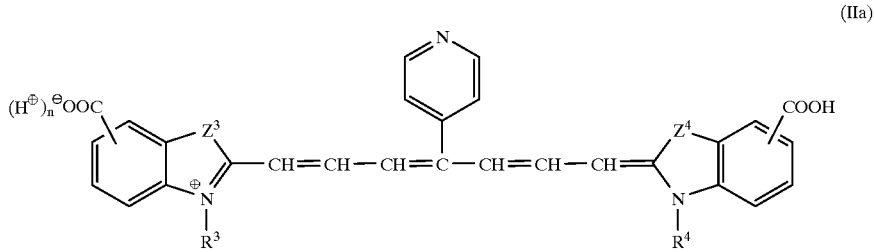

(IIa)

in which each of $Z^3$ and $Z^4$ independently is —$CR^5R^6$—, —$NR^7$—, —O—, —S— or —Se—, and each of $R^5$, $R^6$ and $R^7$ independently is an alkyl group having 1 to 5 carbon atoms; $R^3$ is an alkyl group having 1 to 20 carbon atoms or a sulfoalkyl group having 1 to 20 carbon atoms; $R^4$ is an alkyl group having 1 to 20 carbon atoms or a salt of a sulfoalkyl group having 1 to 20 carbon atoms; and n is 0 when $R^3$ is an alkyl group, and n is 1 when $R^3$ is a sulfoalkyl group.

3. The heptamethine cyanine compound as defined in claim 1, wherein the compound is represented by the formula (IIb):

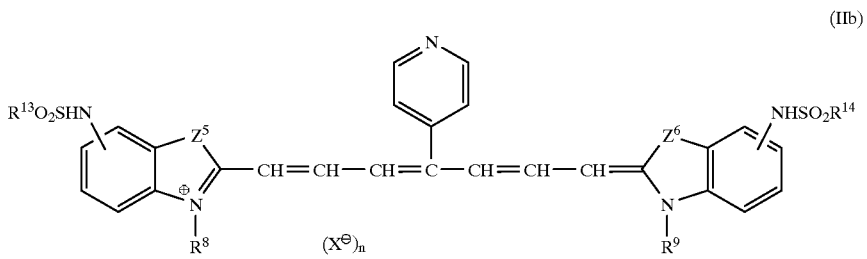

(IIb)

in which each of $Z^5$ and $Z^6$ independently is —$CR^{10}R^{11}$—, —$NR^{12}$—, —O—, —S— or —Se—, and each of $R^{10}$, $R^{11}$ and $R^{12}$ independently is an alkyl group having 1 to 5 carbon atoms; $R^8$ is an alkyl group having 1 to 20 carbon atoms or a sulfoalkyl group having 1 to 20 carbon atoms; $R^9$ is an alkyl group having 1 to 20 carbon atoms or a salt of a sulfoalkyl group having 1 to 20 carbon atoms; each of $R^{13}$ and $R^{14}$ independently is an alkyl group having 1 to 20 carbon atoms; X is an anion; and n is 1 when $R^8$ is an alkyl group, and n is 0 when $R^8$ is a sulfoalkyl group.

4. The heptamethine cyanine compound as defined in claim 1, wherein the compound is represented by the formula (IIc):

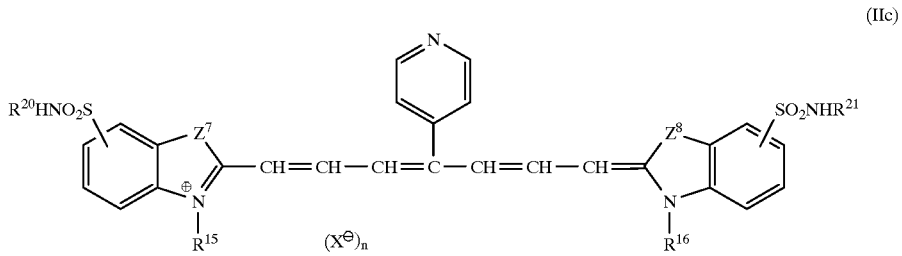

(IIc)

in which each of $Z^7$ and $Z^8$ independently is —$CR^{17}R^{18}$—, —$NR^{19}$, —O—, —S— or —Se—, and each of $R^{17}$, $R^{18}$ and $R^{19}$ independently is an alkyl group having 1 to 5 carbon atoms; $R^{15}$ is an alkyl group having 1 to 20 carbon atoms or a sulfoalkyl group having 1 to 20 carbon atoms; $R^{16}$ is an alkyl group having 1 to 20 carbon atoms or a salt of a sulfoalkyl group having 1 to 20 carbon atoms; each of $R^{20}$ and $R^{21}$ independently is an alkyl group having 1 to 20 carbon atoms; X is an anion; and n is 1 when $R^{15}$ is an alkyl group, and n is 0 when $R^{15}$ is a sulfoalkyl group.

5. The heptamethine cyanine compound as defined in claim 2, wherein the compound is represented by the formula (IIIa):

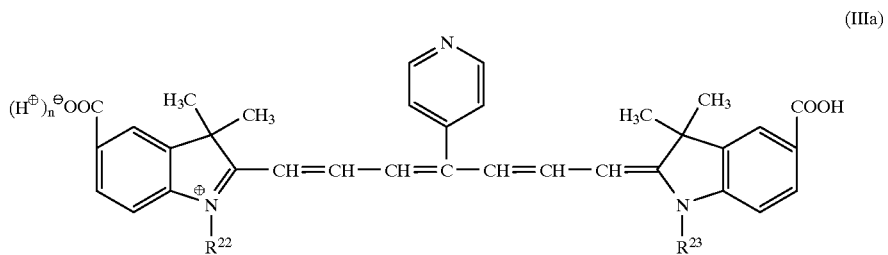

(IIIa)

in which $R^{22}$ is an alkyl group having 1 to 5 carbon atoms or a sulfoalkyl group having 1 to 5 carbon atoms; $R^{23}$ is an alkyl group having 1 to 5 carbon atoms or a salt of a sulfoalkyl group having 1 to 5 carbon atoms; and n is 0 when $R^{22}$ is an alkyl group, and n is 1 when $R^{22}$ is a sulfoalkyl group.

6. The heptamethine cyanine compound as defined in claim 3, wherein the compound is represented by the formula (IIIb):

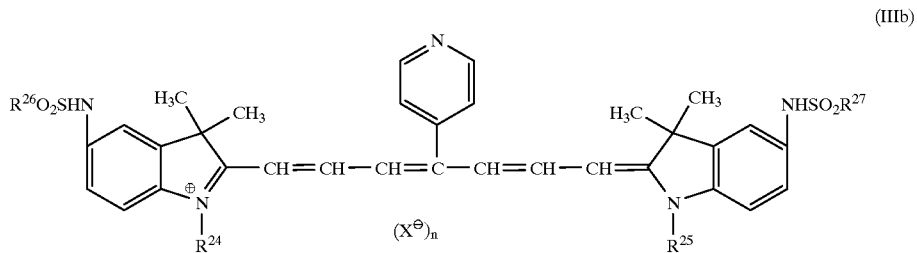

(IIIb)

in which $R^{24}$ is an alkyl group having 1 to 5 carbon atoms or a sulfoalkyl group having 1 to 5 carbon atoms; $R^{25}$ is an alkyl group having 1 to 5 carbon atoms or a salt of a sulfoalkyl group having 1 to 5 carbon atoms; each of $R^{26}$ and $R^{27}$ independently is an alkyl group having 1 to 5 carbon atoms; X is an anion; and n is 1 when $R^{24}$ is an alkyl group, and n is 0 when $R^{24}$ is a sulfoalkyl group.

7. The heptamethine cyanine compound as defined in claim 4, wherein the compound is represented by the formula (IIIc):

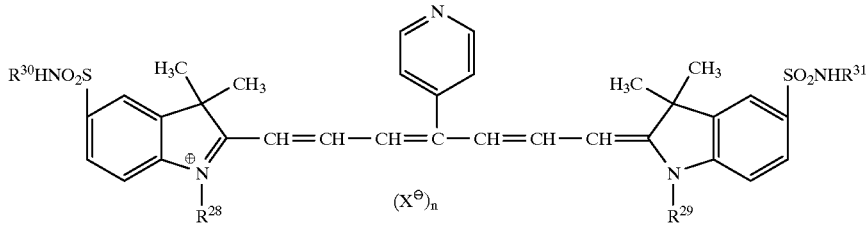

(IIIc)

in which $R^{28}$ is an alkyl group having 1 to 5 carbon atoms or a sulfoalkyl group having 1 to 5 carbon atoms; $R^{29}$ is an alkyl group having 1 to 5 carbon atoms or a salt of a sulfoalkyl group having 1 to 5 carbon atoms; each of $R^{30}$ and $R^{31}$ independently is an alkyl group having 1 to 5 carbon atoms; X is an anion; and n is 1 when $R^{28}$ is an alkyl group, and n is 0 when $R^{28}$ is a sulfoalkyl group.

8. The heptamethine cyanine compound as defined in claim 5, wherein the compound is represented by the formula (IVa):

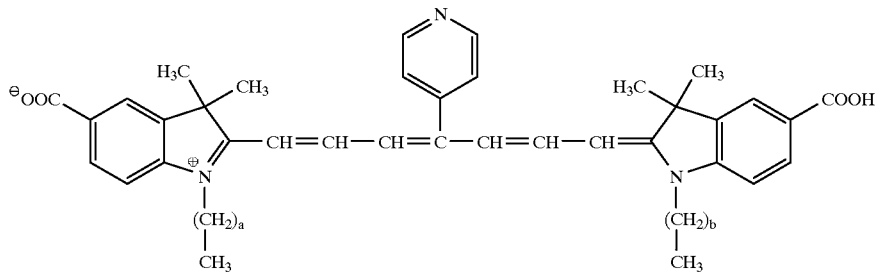

(IVa)

in which each of a and b independently is 0, 1, 2, 3 or 4.

9. The heptamethine cyanine compound as defined in claim 5, wherein the compound is represented by the formula (IVb):

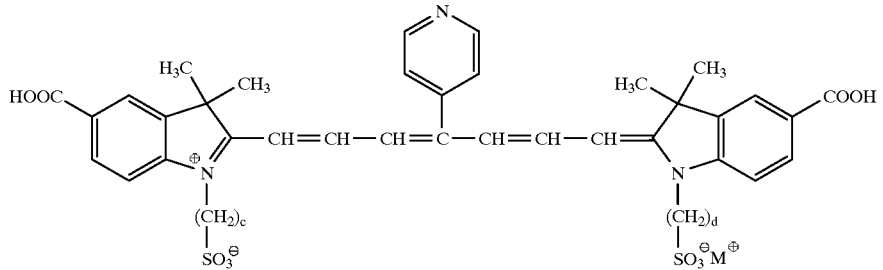

(IVb)

in which each of c and d independently is 1, 2, 3, 4 or 5; and M is a monovalent cation.

10. The heptamethine cyanine compound as defined in claim 6, wherein the compound is represented by the formula (IVc):

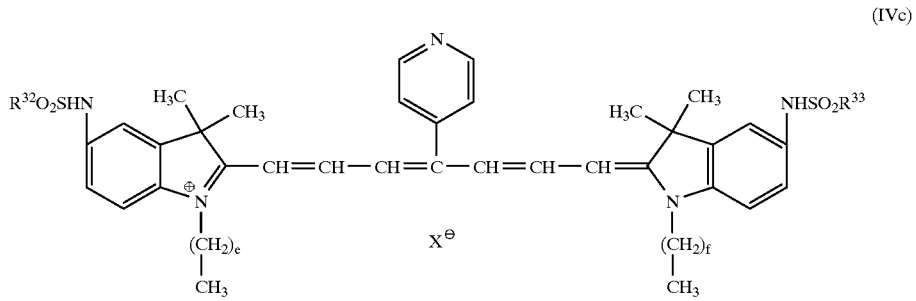

(IVc)

in which each of e and f independently is 0, 1, 2, 3 or 4; X is a monovalent anion; and each of $R^{32}$ and $R^{33}$ independently is an alkyl group having 1 to 5 carbon atoms.

11. The heptamethine cyanine compound as defined in claim 6, wherein the compound is represented by the formula (IVd):

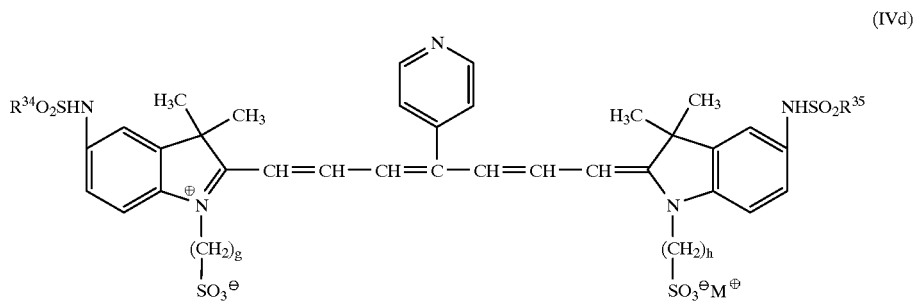

(IVd)

in which each of g and h independently is 1, 2, 3, 4 or 5; M is a monovalent cation; and each of $R^{34}$ and $R^{35}$ independently is an alkyl group having 1 to 5 carbon atoms.

12. The heptamethine cyanine compound as defined in claim 7, wherein the compound is represented by the formula (IVe):

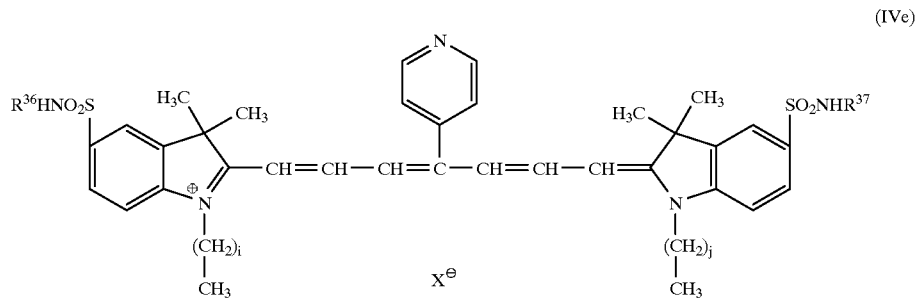

(IVe)

in which each of i and j independently is 0, 1, 2, 3 or 4; X is a monovalent anion; and each of $R^{36}$ and $R^{37}$ independently is an alkyl group having 1 to 5 carbon atoms.

13. The heptamethine cyanine compound as defined in claim 7, wherein the compound is represented by the formula (IVf):

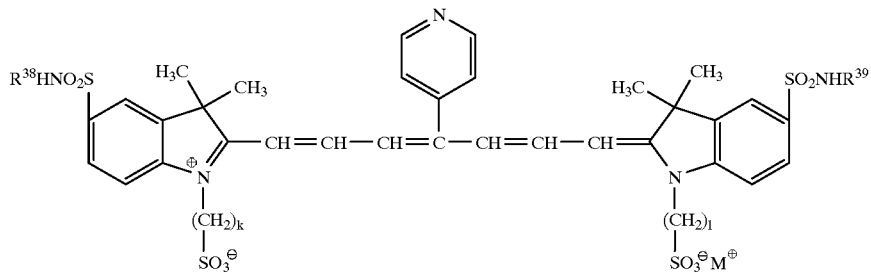
(IVf)
in which each of k and l independently is 1, 2, 3, 4 or 5; M is a monovalent cation; and each of $R^{38}$ and $R^{39}$ independently is an alkyl group having 1 to 5 carbon atoms.
* * * * *